(12) United States Patent
Malinaric et al.

(10) Patent No.: US 12,097,339 B2
(45) Date of Patent: Sep. 24, 2024

(54) SYSTEM AND METHODS OF USING A CATHETER WITH AN ANCHORING MECHANISM

(71) Applicant: Biosense Webster (Israel) Ltd., Yokneam (IL)

(72) Inventors: Jamie Lynn Malinaric, Pasadena, CA (US); John Foley, Yokneam (IL); Dustin R. Tobey, San Dimas, CA (US); Pieter Emmelius Van Niekerk, Monrovia, CA (US); Cesar Fuentes-Ortega, Pasadena, CA (US); Simon Lopez, Yokneam (IL); Paul Suarez, Irwindale, CA (US)

(73) Assignee: Biosense Webster (Israel) Ltd., Yokneam (IL)

( * ) Notice: Subject to any disclaimer, the term of this patent is extended or adjusted under 35 U.S.C. 154(b) by 552 days.

(21) Appl. No.: 17/119,366

(22) Filed: Dec. 11, 2020

(65) Prior Publication Data
US 2021/0196926 A1    Jul. 1, 2021

Related U.S. Application Data

(60) Provisional application No. 62/955,651, filed on Dec. 31, 2019.

(51) Int. Cl.
*A61M 25/01* (2006.01)
*A61M 25/00* (2006.01)

(52) U.S. Cl.
CPC .... *A61M 25/0147* (2013.01); *A61M 25/0075* (2013.01); *A61M 25/0138* (2013.01);
(Continued)

(58) Field of Classification Search
CPC .......... A61M 25/0147; A61M 25/0075; A61M 25/0138; A61M 2025/0076;
(Continued)

(56) References Cited

U.S. PATENT DOCUMENTS

| | | |
|---|---|---|
| 6,690,963 B2 | 2/2004 | Ben-Haim et al. |
| 8,348,888 B2 | 1/2013 | Selkee |

(Continued)

FOREIGN PATENT DOCUMENTS

EP    3398549 A1    11/2018

OTHER PUBLICATIONS

International Search Report dated Jun. 9, 2021 from International Application No. PCT/US2020/070925, 8 pages.

(Continued)

*Primary Examiner* — Amber R Stiles
(74) *Attorney, Agent, or Firm* — Troutman Pepper Hamilton Sanders LLP

(57) ABSTRACT

A catheter includes a catheter body and a distal tip section that includes an elongated member that extends along a longitudinal axis. An anchor mechanism can be disposed along an outer surface of the elongated member and/or within the elongated member in a first configuration. In a second configuration, the anchor mechanism can be configured to extend radially outward with respect to the longitudinal axis to surround at least a portion of the distal tip section.

12 Claims, 21 Drawing Sheets

(52) U.S. Cl.
CPC ............... *A61M 2025/0076* (2013.01); *A61M 2025/0079* (2013.01); *A61M 2025/0163* (2013.01)

(58) Field of Classification Search
CPC .. A61M 2025/0079; A61M 2025/0163; A61M 25/04; A61M 25/0074; A61B 2018/00214; A61B 34/20; A61B 5/6882; A61B 18/1492; A61B 2018/00065; A61B 2018/00267; A61B 2018/00273; A61B 2018/00279; A61B 2018/00285; A61B 2018/00351; A61B 2018/00357; A61B 2018/00577; A61B 2018/00839; A61B 2018/00875; A61B 2018/00904; A61B 2034/2051; A61B 2034/2053; A61B 2090/065; A61B 5/062; A61B 5/068; A61B 5/6856; A61B 5/6885; A61B 5/01
See application file for complete search history.

(56) References Cited

U.S. PATENT DOCUMENTS

| | | | |
|---|---|---|---|
| 8,926,528 | B2 | 1/2015 | Govari et al. |
| 10,569,050 | B1* | 2/2020 | Heesch ............. A61M 25/0074 |
| 2004/0225297 | A1* | 11/2004 | Chen ................. A61M 25/0662 606/108 |
| 2005/0065420 | A1 | 3/2005 | Collins et al. |
| 2006/0036218 | A1* | 2/2006 | Goodson ................ A61M 25/04 604/264 |
| 2006/0229553 | A1* | 10/2006 | Hammack ............. A61M 25/04 604/96.01 |
| 2011/0118546 | A1 | 5/2011 | Dillon et al. |
| 2012/0078078 | A1* | 3/2012 | MacAdam ........... A61B 5/6858 600/381 |
| 2013/0085360 | A1* | 4/2013 | Grunewald ............ A61B 5/287 600/374 |
| 2014/0114246 | A1* | 4/2014 | Kapadia ............. A61B 17/3478 604/116 |
| 2015/0282966 | A1* | 10/2015 | Kelly .................... A61M 25/04 623/1.23 |
| 2018/0028790 | A1* | 2/2018 | Bar-Cohen ........... A61M 25/04 |
| 2018/0220992 | A1* | 8/2018 | Gifford, III .............. A61B 8/06 |
| 2018/0256247 | A1 | 9/2018 | Govari et al. |
| 2020/0015693 | A1 | 1/2020 | Beeckler et al. |
| 2020/0360666 | A1* | 11/2020 | Killeen ............... A61M 25/0147 |
| 2021/0186428 | A1* | 6/2021 | Miller ................... A61L 29/041 |

OTHER PUBLICATIONS

Written Opinion dated Jun. 9, 2021 from International Application No. PCT/US2020/070925, 13 pages.

IPRP dated Jul. 5, 2022 from International Application No. PCT/US2020/070925, 12 pages.

* cited by examiner

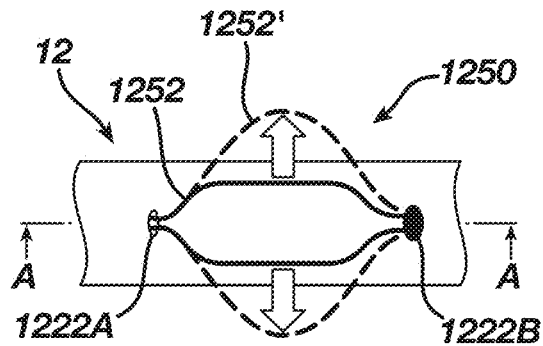
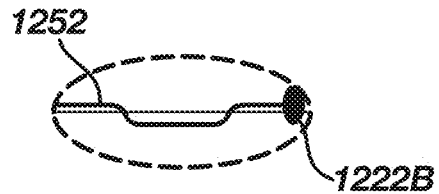
FIG. 17A  FIG. 17B
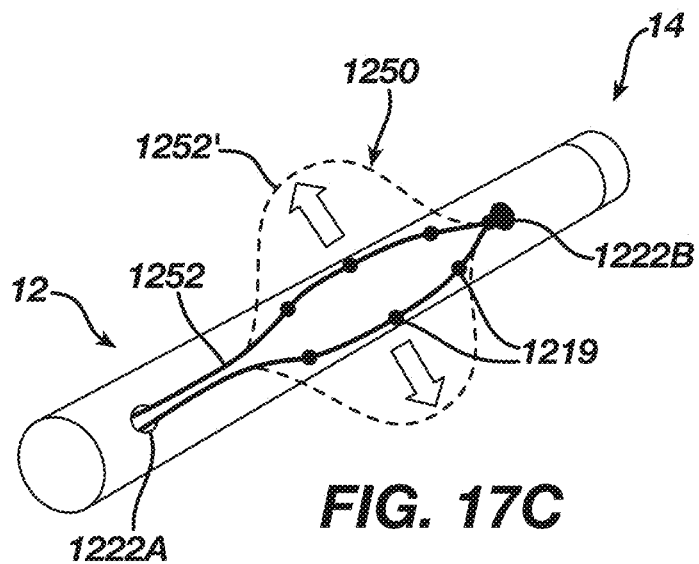
FIG. 17C
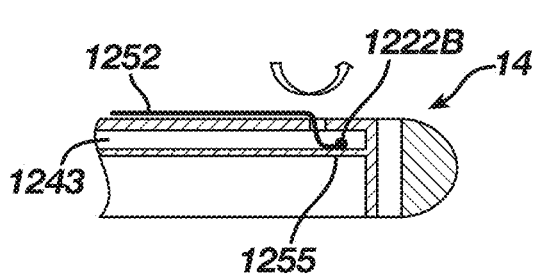
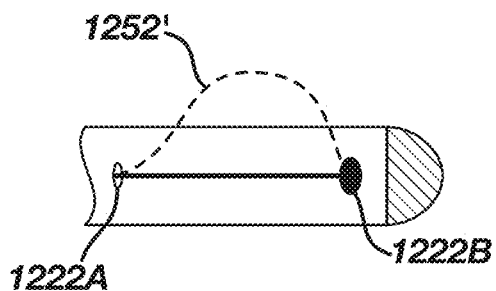
FIG. 17D  FIG. 17E

SYSTEM AND METHODS OF USING A CATHETER WITH AN ANCHORING MECHANISM

CROSS-REFERENCE TO RELATED APPLICATION

The present application claims benefit of priority to U.S. Provisional Patent Application No. 62/955,651 filed Dec. 31, 2019. The entire contents of which are hereby incorporated by reference.

FIELD

This disclosure relates to systems and approaches to anchoring a catheter into a blood vessel of a patient.

BACKGROUND

Catheter technology is widely utilized to diagnose many abnormalities, to treat vascular disease, to perform vascular interventions, to deliver devices to occlude vessels, and to focally deliver agents to tissues, among other uses. Stability of the catheter tip can be significant to the success of a particular procedure associated with any of the foregoing types of catheters.

For example, in a coronary angioplasty, stent placement with a guide catheter can lead to backing out by the catheter when a guide wire or the interventional device catheter is advanced through the narrowed lesion, or attempts are made to advance through the narrowed lesion, because of the resistance caused by the lesion. Without sufficient anchoring, repeated attempts to cross the lesion can be required, among other issues.

In addition, with carotid artery lesions, acute angles can complicate stent delivery as the guide catheters tend to back out of a vessel orifice.

Finally, electrode catheters have been used to stimulate and map electrical activity in the heart and to ablate sites of aberrant electrical activity. In use, the electrode catheter is inserted into a major vein or artery, e.g., femoral artery, and then guided into the chamber of the heart which is of concern. Within the heart, the ability to control the exact position and orientation of the catheter tip is critical. Any instability with an electrode catheter can therefore affect results of a related procedure (e.g., unreliable results of cardiac mapping) and thus be significant to the success of a particular procedure.

The solution of this disclosure resolves these and other problems of the art.

SUMMARY

Accordingly, the inventors of this disclosure have recognized that there is a need for a catheter capable of effectively anchoring to a vessel wall, such as the coronary sinus wall. In some examples, a catheter is disclosed. In some examples, the catheter can include a catheter body and a distal tip section comprising an elongated member that extends along a longitudinal axis. An anchor mechanism can be disposed along an outer surface of the elongated member and/or within the elongated member in a first configuration. In a second configuration, the anchor mechanism is configured to extend radially outward with respect to the longitudinal axis to surround at least a portion of the distal tip section.

In some examples, one or more wires can be included that exit a distal end of the catheter on or adjacent the distal tip section to form one or more wire anchors. A distal end of the one or more wires can be fixedly attached to the distal tip section. A puller wire can be configured to pull the one or more wires and/or the distal tip section causing the anchor mechanism to transition from the first to the second configuration.

In some examples, the anchor mechanism is activated by the puller wire pulling the one or more wires effectively reducing a distance between the distal and proximal end of corresponding one or more wires.

In some examples, when the puller wire is in a neutral location, the one or more wires are axially aligned along the catheter body.

In some examples, the anchor mechanism transitioning from first to second configurations causes the catheter to bow or flex outwardly in the second configuration and deliver a predetermined force with the vessel wall.

In some examples, the one or more wires of the one or more wire anchors is shape-set.

In some examples, the one or more wires is asymmetrically positioned on only one side of an outer surface of the catheter to anchor against the blood vessel wall.

In some examples, the one or more wires in the second configuration includes a diameter at least two times greater than an outer diameter of the catheter.

In some examples, the one or more wires in the second configuration include a diameter at least four times greater than an outer diameter of the catheter.

In some examples, the one or more wires in the second configuration include an atraumatic surface that contacts the vessel wall.

In some examples, the one or more wires are retractable back into the catheter from the second configuration.

In some examples, the one or more wires are configured to exit the distal end of the catheter multiple times and secured at or adjacent the tip section.

In some examples, the one or more wires are deployed to the second configuration by being advanced from a proximal handle operatively coupled to the puller wire.

In some examples, the anchor mechanism includes a sheath that exits an opening of the catheter on or adjacent the distal tip section. An extendable member can be included that telescopes into and out of sheath between the first and second configurations to form one or more wire anchors, a distal end of the extendable member being fixedly attached to the distal tip section.

In some examples, the sheath includes a lumen with an inner diameter greater than an outer diameter of the extendable member.

In some examples, proximally moving the sheath and/or distally moving the extendable member a first distance causes the extendable member to expand radially, outwardly between one or more expanded states of corresponding diameters greater than an outer diameter of the catheter.

In some examples, the opening includes a slit that forms a one-way valve in the outer surface of catheter.

In some examples, the opening includes an elliptical shape.

In some examples, the opening includes a rectangular shape.

In some examples, the anchor mechanism in the second configuration includes a diameter at least two times greater than an outer diameter of the catheter.

In some examples, the anchor mechanism in the second configuration includes a diameter at least four times greater than an outer diameter of the catheter.

In some examples, the anchor mechanism includes a plurality of expandable members adjacent the distal tip section. A void can be positioned between respective expandable members. In this respect, moving portions of the catheter body proximal of expandable members while the distal tip section is relatively stationary causes respective expandable members to expand radially outwardly to the second configuration greater than an outer diameter of the catheter body.

In some examples, each of the expandable members can be radially arranged in series about the longitudinal axis.

In some examples, each of the expandable members is independently movable to the second configuration.

In some examples, each of the expandable members includes a respective push wire configured to be independently translated distally to the second configuration.

In some examples, each of the expandable members includes same or similar diameters in the second configuration.

In some examples, each of the expandable members expand outwardly in a balloon-manner in the second configuration to form a porous anchoring balloon.

In some examples, each of the expandable members includes different diameters in the second configuration.

In some examples, the expandable members collectively form a substantially planar or flat shape.

In some examples, the expandable members collectively form a non-circular shape.

In some examples, one or more of the expandable members includes a plurality of electrodes separately positioned therealong, the plurality of electrodes configured to be read simultaneously at different vessel depths and radial positions In some examples, the anchor mechanism includes a plurality of wire members distally axially extended from a convergence along the catheter body and terminate in one or more variable loop lassos fixedly wrapped at or adjacent the distal tip section. Pushing the plurality of wire members causes the wire members to expand outwardly to the second configuration.

In some examples, a pusher wire is included that proximally extends from the convergence through an opening in a lumen of the catheter body. The pusher wire is configured to actuate the anchor mechanism between first and second configurations.

In some examples, a pusher wire is included that proximally extends generally along an outer surface of the catheter body.

In some examples, the plurality of wire members, in the second configuration, is configured to expand outwardly between a plurality of different orientations and/or diameters.

In some examples, at least two of the plurality of wire members, in the second configuration, are generally orthogonal with respect to the other.

In some examples, at least two of the plurality of wire members, in the second configuration, form a generally obtuse angle with respect to the other.

In some examples, the anchor mechanism includes a plurality of wire members distally axially extended along the catheter body and terminate fixedly attached at or adjacent the distal tip section. Pushing the plurality of wire members causes the wire members to expand outwardly away from the other to the second configuration.

In some examples, a pusher wire is included that proximally extends from a proximal end of the plurality of wire members.

In some examples, a pusher wire is included that proximally extends from within the catheter body through an opening in a lumen of the catheter body.

In some examples, each of the plurality of wire members deliver an outward radial force to the vessel wall in the second configuration, each of the plurality wire members being radially arranged about the catheter body.

In some examples, the plurality of wire members is bowed away from the other in the first configuration in a generally elliptical shape.

In some examples, the catheter body includes at least two inner lumens, wherein at least one of the two inner lumens is configured to fixedly receive a distal end of the plurality of wire members.

In some examples, the elongated member includes a circumferential opening disposed on an outer surface of the elongated member, the anchor mechanism being configured to extend outward radially from the circumferential opening of the elongated member.

In some examples, the catheter can include a catheter body, and a distal tip section that includes an elongated member that extends along a longitudinal axis, the elongated member comprising a circumferential opening disposed on an outer surface of the elongated member. An anchor mechanism is disposed within the elongated member in a first configuration. The anchor mechanism is configured to extend outward with respect to the longitudinal axis from a circumferential opening of the elongated member to surround at least a portion of the distal tip section in a second configuration.

In some examples, the anchor mechanism can include at least one of a first configuration within a lumen and the first configuration coextensive with the lumen of the catheter and a second configuration external to the catheter to anchor against a blood vessel wall.

In some examples, the catheter includes one or more electrodes and the catheter is an electrode catheter.

In some examples, the anchor mechanism includes a variable loop lasso.

In some examples, the anchor mechanism is extendable from a catheter lumen through an opening in an outer surface of the catheter when moving from the first to the second configuration.

In some examples, the variable loop lasso includes one or more wires being movable from the first configuration to the second configuration by being distally translated through the opening.

In some examples, the variable loop lasso is actuatable from the first configuration to the second configuration by expanding and/or contracting the variable loop lasso around the catheter body in a python or boa-like manner.

In some examples, the variable loop lasso includes one or more wires comprising a variable diameter loop and configured to push against the vessel wall in the second configuration.

In some examples, the variable loop lasso is being movable between a plurality of different second configurations with different diameters.

In some examples, the anchor mechanism includes one or more wires shaped in a round, spiral, or helical form and extended from an opening in a distal end of the catheter in the second configuration.

In some examples, in the second configuration, the anchor mechanism is axially aligned with a longitudinal axis of the catheter.

In some examples, in the second configuration, the anchor mechanism is attached to only one side of an outer surface of the catheter to be pushed against the blood vessel wall.

In some examples, the catheter includes a coiled wire attached to the variable loop lasso, the coiled wiring being twistable to cause the variable loop lasso to deploy through the opening and anchor to the vessel wall.

In some examples, the coiled wire is attached to a proximal end of the variable loop lasso.

In some examples, the coiled wire is axially connected to a catheter lumen of the catheter body.

In some examples, the coiled wire is axially connected to the catheter, the coiled wire being wrapped around an outer surface of the catheter body. In some examples, the coiled wire includes one or more twists.

In some examples, the anchor mechanism includes one or more strips connected to an outer surface of the catheter, the one or more strips being configured to bunch up and outwardly extend when one or more portions of the distal tip section are withdrawn towards one or more portions of the catheter proximal thereof.

In some examples, the one or more strips are configured to outwardly extend to a diameter at least two times an outer diameter of the catheter.

In some examples, the one or more strips are configured to outwardly extend to at least two opposing sides of the catheter in a balloon-like manner.

In some examples, the one or more strips are configured to outwardly extend through a plurality of slits of an outer surface of the catheter.

In some examples, the one or more strips are actuated to the second configuration by one or more pull members actuatable by an end-user operatively connected to the one or more strips.

In some examples, the one or more strips are positioned on only one side of the catheter and configured to push into the blood vessel on that only one side.

In some examples, the one or more strips are positioned between a plurality of electrodes of the distal tip section. In some examples, the electrodes include at least an ablating electrode. In some examples, the electrodes include at least a recording electrode. In some examples, the electrodes include at least a sensing electrode.

In some examples, a region surrounding the one or more strips comprising a soft pliable plastic comprising an elastomer.

In some examples, a region surrounding the one or more strips comprising a soft pliable plastic comprising Pebax® (polyether block amide).

In some examples, the one or more strips include polyether ether ketone (PEEK).

In some examples, the catheter is withdrawn a predetermined distance to cause the strips to move to the second configuration. In some examples, the predetermined distance comprising a 1:1 ratio with a radial extent of the strips in the second configuration.

In some examples, the anchor mechanism includes a plurality of strips connected to an outer surface of the catheter, the strips being configured to bunch up and outwardly extend when one or more portions of the distal tip section are withdrawn towards one or more portions of the catheter proximal thereof. In some examples, the strips are radially separated (e.g., radially separated equally about a longitudinal axis of the catheter). In some examples, the strips are configured to outwardly extend to a diameter at least two times an outer diameter of the catheter. In some examples, the strips are configured to outwardly extend to at least two opposing sides of the catheter in a balloon-like manner. In some examples, the strips are configured to outwardly extend through a plurality of slits of an outer surface of the catheter. In some examples, the strips are actuated to the second configuration by one or more pull members actuatable by an end-user operatively connected to the strips.

In some examples, the strips are positioned between a plurality of electrodes of the distal tip section. In some examples, the electrodes include at least an ablating electrode. In some examples, the electrodes include at least a recording electrode. In some examples, the electrodes include at least a sensing electrode.

In some examples, a region surrounds the strips and includes a soft pliable plastic comprising an elastomer.

In some examples, a region surrounds the strips and includes a soft pliable plastic comprising Pebax® (e.g., polyether block amide).

In some examples, the strips include polyether ether ketone (PEEK).

In some examples, the catheter is withdrawn a predetermined distance to cause the strips to move to the second configuration. In some examples, the predetermined distance comprising a 1:1 ratio with a radial extent of the strips in the second configuration.

In some examples, the distal tip section of the catheter is being retractable to cause the anchor mechanism to move to the second configuration. The anchor mechanism in this embodiment includes a plurality of walls, a first wall of the plurality of walls being a pliable and a second wall of the plurality of walls formed as strips more rigid than the first wall, the strips being outwardly expandable when the distal tip section is withdrawn causing the first wall to crumple in on itself.

In some examples, the plurality of walls is positioned between a plurality of electrodes positioned on the distal tip section.

In some examples, the first wall includes a soft pliable plastic that has an elastomer.

In some examples, the first wall includes a soft pliable plastic that has Pebax® (e.g., polyether block amide).

In some examples, the second wall includes polyether ether ketone (PEEK).

In some examples, the catheter includes a sensor to detect movement of the catheter.

In some examples, the catheter includes a sensor to detect whether the anchor mechanism is anchored to the vessel wall.

In some examples, the anchor mechanism is a balloon that is expandable to a radial extent greater than an outer diameter of the catheter in the second configuration, the balloon configured to expand and anchor with the vessel wall without occluding the blood vessel.

In some examples, the balloon is collapsible within the catheter in the first configuration.

In some examples, the balloon includes an expandable section formed with a wall of the catheter at least one of in or adjacent to the distal tip section, the expandable section being softer than surrounding wall sections of the catheter and configured to expand outwardly and apply pressure to the vessel wall in the second configuration.

In some examples, the balloon is positioned in or adjacent the distal tip section and in fluid communication with a pressure lumen within the catheter.

In some examples, the balloon is configured to expand outwardly from only one side of the catheter.

In some examples, the balloon is configured to expand outwardly to a radial extent at least two times an outer diameter of the catheter.

In some examples, the anchor mechanism is expandable along a length of the distal tip section.

In some examples, the anchor mechanism includes one or more wires that exits a distal end of the catheter on or adjacent the distal tip section to form one or more wire anchors.

In some examples, the one or more wires of the one or more wire anchors is shape-set.

In some examples, the one or more wire anchors is positioned on only one side of an outer surface of the catheter to anchor against the blood vessel wall.

In some examples, the one or more wire anchors includes the one or more wires bulged with at least one anchoring bump. In some examples, the at least one anchoring bump in the second configuration includes a diameter at least two times greater than an outer diameter of the catheter. In some examples, the at least one anchoring bump includes an atraumatic surface that contacts the vessel wall. In some examples, the at least one anchoring bump includes a fish-hook shaped surface to anchor to the vessel wall.

In some examples, the one or more wires are retractable back into the catheter from the second configuration. In some examples, the one or more wires are configured to exit the distal end of the catheter multiple times and secured at or adjacent the tip section. In some examples, the one or more wires are deployed to the second configuration by being advanced from a proximal shaft or a proximal handle operatively coupled to a proximal end of the catheter. In some examples, the one or more wires are deployed to the second configuration from a single puller mechanism retractable into a catheter body of the catheter between uses.

In some examples, a method is disclosed to anchor a catheter to a blood vessel of a treatment site. The method can include delivering the catheter to the treatment site, the catheter comprising a catheter body and a distal tip section comprising an anchor mechanism deployable from the distal tip section, the anchor mechanism comprising a first configuration within or coextensive with a lumen of the catheter and an second configuration external to the catheter to anchor against the vessel wall, deploying the anchor mechanism, and anchoring the anchor mechanism to the blood vessel wall. In some examples, the blood vessel wall is a coronary sinus wall. In some examples, the catheter of the method includes one or more electrodes and is an electrode catheter.

In some examples, the anchor mechanism of the method includes one or more wires shaped in a round, spiral, or helical form and extended from an opening in a distal end of the catheter in the second configuration.

In some examples, the anchor mechanism of the method includes a variable loop lasso.

In some examples, the method includes extending the anchor mechanism from a catheter lumen through an opening in an outer surface of the catheter when deploying the anchor mechanism from the first to the second configuration.

In some examples, the anchor mechanism of the method includes a variable loop lasso with one or more wires. The method in this embodiment includes distally translating the anchor mechanism through the opening thereby causing the anchor mechanism to move from the first configuration to the second configuration.

In some examples, the anchor mechanism of the method includes a variable loop lasso with one or more wires with a variable diameter loop. The method in this embodiment includes pushing, by the variable loop lasso in the second configuration, against the vessel wall.

In some examples, the method includes moving the variable loop lasso being between a plurality of different second configurations with different diameters.

In some examples, the method includes axially aligning the anchor mechanism with a longitudinal axis of the catheter.

In some examples, the method includes positioning the anchor mechanism on only one side of an outer surface of the catheter and pushing, by the anchor mechanism in the second configuration, against the blood vessel wall.

In some examples, the method includes attaching a coiled wire attached to the variable loop lasso and twisting the coiled wire thereby causing cause the variable loop lasso to deploy through the opening and anchor to the vessel wall.

In some examples, the method includes attaching the coiled wire being to a proximal end of the variable loop lasso.

In some examples, the method includes axially connecting the coiled wire to a catheter lumen of the catheter body.

In some examples, the method includes axially connecting and wrapping the coiled wire to the catheter body, the coiled wire being wrapped around an outer surface of the catheter body. The coiled wire can include one or more twists and/or loops.

In some examples, the anchor mechanism of the method includes one or more strips connected to an outer surface of the catheter. The method in this embodiment includes withdrawing one or more portions of the distal tip section towards one or more portions of the catheter proximal thereof thereby bunching up and outwardly extending the one or more strips. The method can also include outwardly extending the one or more strips to a diameter at least two times an outer diameter of the catheter. The method can also include outwardly extending the one or more strips to at least two opposing sides of the catheter in a balloon-like manner. The method can also include outwardly extending the one or more strips through a plurality of slits of an outer surface of the catheter. The method can also include actuating the one or more strips to the second configuration by pulling or translating one or more pull members operatively connected to the one or more strips.

In some examples, the method can include positioning the one or more strips on only one side of the catheter and pushing, by the one or more strips of the anchor mechanism in the second configuration, against the blood vessel wall on that only one side.

In some examples, the method can include positioning the one or more strips between a plurality of electrodes of the distal tip section.

In some examples, the method can include positioning a region surrounding the one or more strips with a soft pliable plastic comprising an elastomer.

In some examples, the method can include positioning a region surrounding the one or more strips with soft pliable plastic comprising Pebax® (polyether block amide).

In some examples, the method can include withdrawing the catheter a predetermined distance causing one or more strips to move to the second configuration. The predetermined distance can include a 1:1 ratio with a radial extent of one or more strips in the second configuration.

In some examples, the anchor mechanism of the method includes a plurality of strips connected to an outer surface of the catheter. The method can include withdrawing one or more portions of the distal tip section towards one or more portions of the catheter proximal thereof thereby bunching up and outwardly extending the strips. The method can also include radially separating the strips along an outer surface of the catheter. The strips can be radially separated equally. The method can also include outwardly extending the strips to a diameter at least two times an outer diameter of the catheter. The method can also include outwardly extending the strips to at least two opposing sides of the catheter in a balloon-like manner.

In some examples, the method includes outwardly extending the strips through a plurality of slits of an outer surface of the catheter. The method can also include actuating the strips to the second configuration by pulling or translating one or more pull members operatively connected to the strips. The method can also include positioning the strips on only one side of the catheter, and pushing, by the strips of the anchor mechanism in the second configuration, against the blood vessel wall on that only one side. The method can also include positioning the strips between a plurality of electrodes of the distal tip section.

In some examples, the method includes positioning a region surrounding the strips with a soft pliable plastic comprising an elastomer.

In some examples, the method includes withdrawing the catheter a predetermined distance causing the strips to move to the second configuration. The predetermined distance can include a 1:1 ratio with a radial extent of the strips in the second configuration.

In some examples, the method includes detecting, by a sensor of the catheter, movement of the catheter.

In some examples, the method includes detecting, by a sensor of the catheter, whether the anchor mechanism is anchored to the vessel wall.

In some examples, the method includes determining a position and orientation of the anchor mechanism by generating a plurality of AC magnetic fields, each AC magnetic fields being at a different frequency, sensing the AC magnetic fields at a plurality of sensors proximate the distal tip section, and computing dimensions of position and orientation of a portion of the distal tip section responsive to signals representative of the generated magnetic fields and the sensed magnetic fields.

In some examples, the method includes determining a position and orientation of the distal tip section by generating a plurality of AC magnetic fields, each AC magnetic fields being at a different frequency, sensing the AC magnetic fields at a plurality of sensors proximate the distal tip section, and computing dimensions of position and orientation of a portion of the distal tip section responsive to signals representative of the generated magnetic fields and the sensed magnetic fields.

In some examples, the method includes generating, by at least one field generator, an externally applied magnetic field to establish a frame of reference, positioning a plurality of sensors comprising single-axis coils around the distal tip section, each single-axis coils being fixed at different, respective points about the distal tip section, and determining dimensional translational and orientational coordinates of the single-axis coils by processing signals from the single-axis coils.

In some examples, the method includes positioning one or more electrodes on the distal tip section at known fixed locations with respect to at least one of said single-axis coils, a location of the respective electrode being derived from the dimensional translational and orientation coordinates of the single-axis coils.

In some examples, the method includes deflecting the tip section in response to moving one or more puller wires.

In some examples, the method includes moving, by a steering assembly, the one or more puller wires.

In some examples, the method includes deflecting the tip section in the direction of the off-axis lumen in which a respective puller wire extends.

In some examples, the method includes assembling the catheter with a control handle comprising a deflection knob, and adjusting, by rotating the deflection knob, a tip deflection orientation of the tip section.

In some examples, the method includes extending a segment of the one or more puller wires drawn by a pulley for deflection at an angle of less than about 7 degrees with respect to a longitudinal axis.

In some examples, the anchor mechanism of the method includes a balloon, whereby the step of anchoring further includes expanding the balloon to a radial extent greater than an outer diameter of the catheter in the second configuration thereby anchoring the anchor mechanism to the vessel wall without occluding the blood vessel.

In some examples, the method can include collapsing the balloon within the catheter in the first configuration.

In some examples, the method can include forming the balloon with an expandable section of a wall of the catheter in or adjacent the distal tip section, the expandable section being softer than surrounding wall sections of the catheter and configured to expand outwardly and apply pressure to the vessel wall in the second configuration.

In some examples, the method can include positioning the balloon in or adjacent the distal tip section and in fluid communication with a pressure lumen within the catheter.

In some examples, the method can include expanding the balloon outwardly from only one side of the catheter.

In some examples, the method can include expanding the balloon outwardly to a radial extent at least two times an outer diameter of the catheter.

In some examples, the method can include expanding the balloon outwardly along a length of the distal tip section.

In some examples, the anchor mechanism of the method includes one or more wires. The method in this embodiment includes the one or more wires exiting a distal end of the catheter on or adjacent the distal tip section to form one or more wire anchors of the anchor mechanism. In some examples, the method can include shape setting the one or more wires of the one or more wire anchors. In some examples, the method can include positioning the one or more wire anchors on only one side of an outer surface of the catheter to anchor against the blood vessel wall.

In some examples, the method can include bulging out the one or more wire anchors to form at least one anchoring bump. The at least one anchoring bump can include a diameter in the second configuration at least two times greater than an outer diameter of the catheter. The at least one anchoring bump can include an atraumatic surface that contacts the vessel wall. The at least one anchoring bump can include a fish-hook shaped surface to anchor to the vessel wall.

In some examples, the method can include retracting the one or more wires back into the catheter from the second configuration.

In some examples, the method can include exiting and retracting the one or more wires back into the catheter multiple times.

In some examples, the step of deploying the anchor mechanism includes advancing the one or more wires from a proximal shaft or a proximal handle operatively coupled to a proximal end of the catheter.

In some examples, the step of deploying the anchor mechanism includes advancing the one or more wires to the second configuration from a single puller mechanism retractable into a catheter body of the catheter between uses.

The present disclosure will be more fully understood from the following detailed description of embodiments thereof, taken together with the drawings.

BRIEF DESCRIPTION OF THE DRAWINGS

While the specification concludes with claims, which particularly point out and distinctly claim the subject matter described herein, it is believed the subject matter will be better understood from the following description in conjunction with the accompanying drawings, in which like numerals indicate like structural elements and features in various figures. The drawings are not necessarily to scale, emphasis instead being placed upon illustrating principles of the disclosure. The figures depict one or more implementations of the inventive devices, by way of example only, not by way of limitation.

FIG. 17A is a close-up top view of a portion of a tip section of another example catheter of this disclosure.

FIG. 17B is a close-up side view of the portion of the tip section of FIG. 17A.

FIG. 17C is a close-up perspective view of the portion of the tip section of FIG. 17A.

FIG. 17D is a close-up plan view of the portion of the tip section of FIG. 17A in a first orientation.

FIG. 17E is a close-up plan view of the portion of the tip section of FIG. 17A in a second orientation.

DETAILED DESCRIPTION

As used herein, the terms "about" or "approximately" for any numerical values or ranges indicate a suitable dimensional tolerance that allows the part or collection of components to function for its intended purpose as described herein. More specifically, "about" or "approximately" may refer to the range of values ±20% of the recited value, e.g. "about 90%" may refer to the range of values from 71% to 99%.

As used herein, a "subject" or "patient", including a blood vessel from a subject or a patient, may refer to any applicable human patient as well as any mammal, veterinarian animal, livestock animal or pet type animal, etc. As an example, the animal may be a laboratory animal specifically selected to have certain characteristics similar to a human (e.g., rat, dog, pig, rabbit, monkey, or the like).

As used herein, "operator" may include a doctor, surgeon, or any other individual or instrumentation associated with the medical procedure used with the device(s) of this disclosure.

Figure 1A:
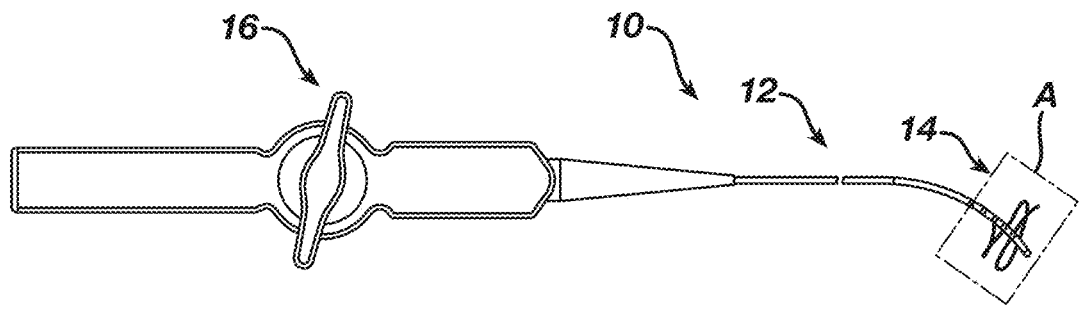
FIG. 1A is a side view of an embodiment of on example catheter of this disclosure.
Figure 1B:
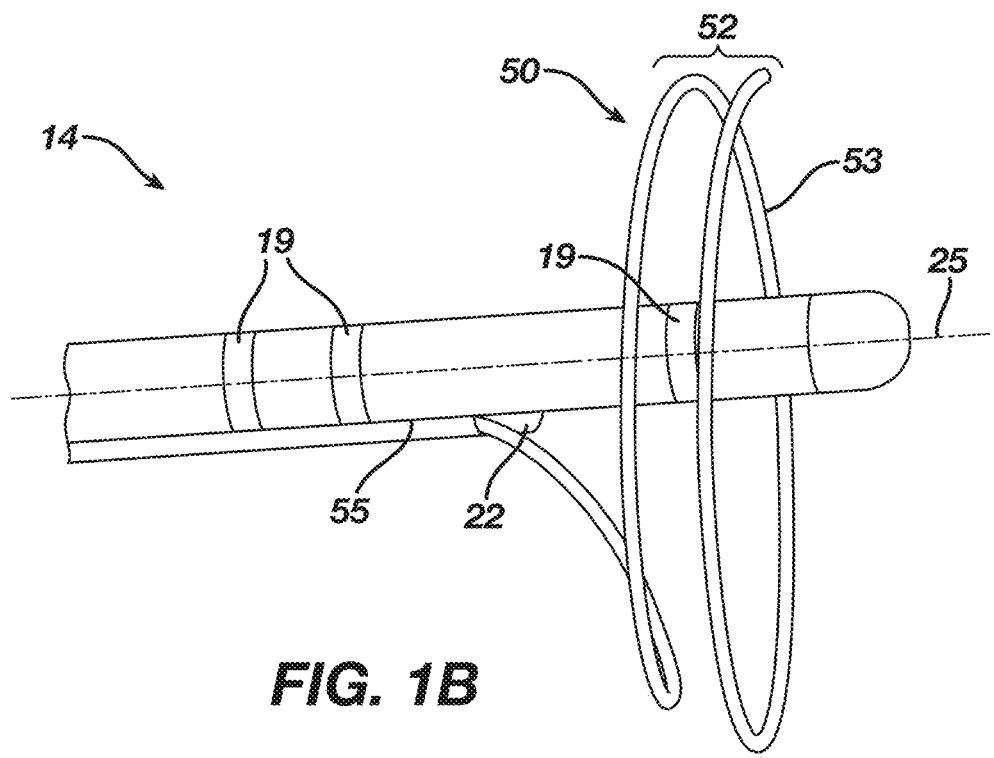
FIG. 1B is a close-up side view of the tip section of FIG. 1A taken along section A-A.

The present disclosure generally relates to a catheter with one or more anchor mechanisms to stabilize a distal tip section of the catheter when in use. Turning to FIGS. 1A-1B, a steerable bidirectional electrode catheter 10 is shown. The catheter 10 can include an elongated catheter body 12 having proximal and distal ends, a tip section 14 at the distal end of the catheter body 12, and a control handle 16 at the proximal end of the catheter body 12. FIG. 1B is a close-up side view of the tip section 14 taken along section A-A. Body 12 can include an elongated tubular construction having a single axial or central lumen. The catheter body 12 can be flexible (e.g., bendable, but substantially non-compressible along its length). The catheter body 12 can be of any suitable construction and made of any suitable material.

Tip section 14 can comprise a longitudinal axis 25 and be uni- or bi-directionally deflected off the axis therefrom. Tip section 14 can also include one or more electrodes 19 selectively positioned and/or separated about tip section 14. Tip section 14 can also include an anchor mechanism 50 positioned and/or deployable therealong. It is understood that while an electrode catheter is shown in the herein provided figures, other types of catheters are contemplated for use with the herein disclosed anchor mechanisms. Mechanism 50 can be disposed within and/or along body 12 in a first configuration (e.g., a collapsed configuration). Mechanism 50 can be configured to extend outward with respect to the longitudinal axis from the circumferential opening of the elongated member to surround at least a portion of the distal tip section in a second configuration (e.g., an expanded configuration).

Figure 2:
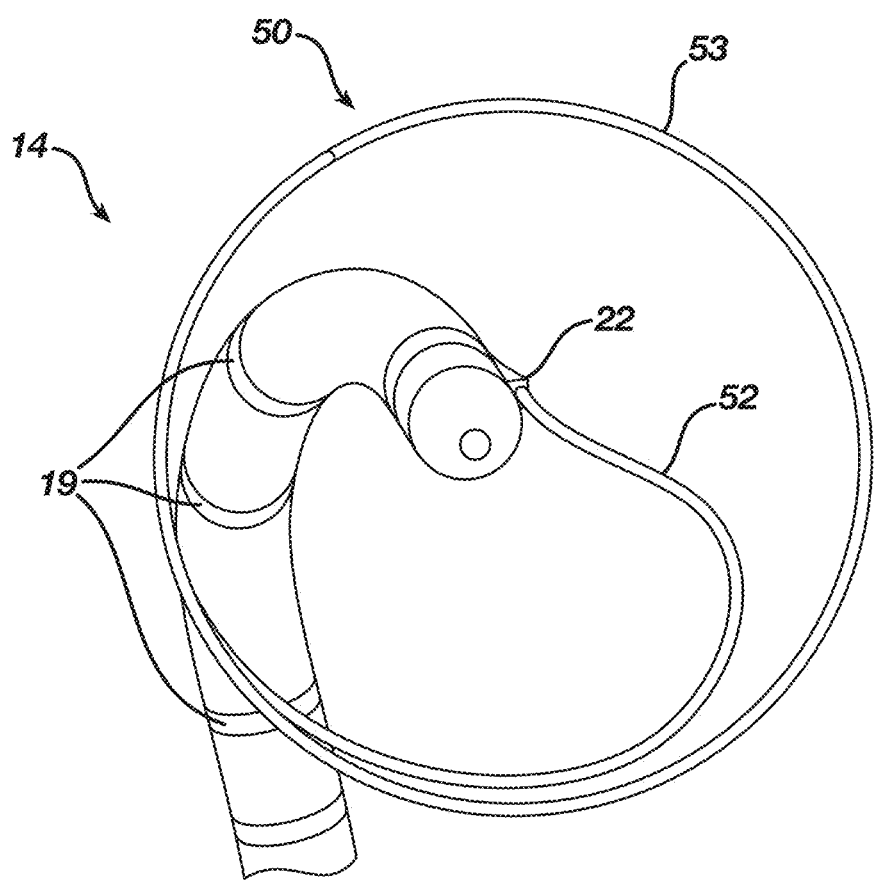
FIG. 2 is a close-up forward plan view of the example catheter of FIG. 1A-FIG. 1B.

In the depicted example of FIGS. 1A-1B, mechanism 50 can be positionable inside body 12, including at or about tip section 14 (e.g., in a lumen therein) and once deployed, can comprise one or more wires 52. FIG. 2 is a close-up forward plan view of catheter 10 of FIGS. 1A-1B. As shown, wires 52 can be in a shape-set configuration, such as in the shape of a variable lasso or otherwise rounded a round, spiral, or helical form. In some examples, one or more wires 52 can include one or more curved sections or loops 53 that can be generally thin and flexible. The one or more loops 53 can be disposed around section 14 but leave a space therebetween through which blood may flow even when wires 52 contact a corresponding vessel wall. In this regard, wires 52 that form the one or more loops 53 facilitate anchoring to the vessel wall while avoiding occluding blood flow in the vessel itself. The one or more loop segments 53 of mechanism 50 can be axially aligned with axis 25 or otherwise oriented.

The one or more loop segments 53 can be connected to an elongate base segment 55 proximate the one or more loop segments 53. The curvature of the one or more loop segments 53 formed by one or more wires 52 can be adjustable (e.g., diameter of mechanism 50, distance between loops, length of mechanism 50 in the second configuration, etc.) using the steering and/or control mechanisms (not shown). A radius of any loop segments 53 of mechanism 50 can be adjustable (e.g., between 7-25 mm). In some examples, one or more loops of mechanism 50 can be dimensioned so as to conform to structures such as the ostia of pulmonary veins or the coronary sinus. The one or more loop segments 53 can include an elasticity that is generally constant over at least a portion of its length, for example, because of internal reinforcement of the curved section with a resilient longitudinal member so as to sufficiently anchor mechanism 50 with the vessel wall in the second configuration. The one or more loop segments 53 can be generally thicker and/or stiffer than the remainder of the one or more wire proximal thereto.

More or fewer loops than depicted in FIGS. 1A-1B can be provided as needed or required. The one or more loops of the depicted mechanism 50 can also include variable diameter loop(s) configured to push against the vessel wall in the second configuration. The depicted mechanism 50 can also be configured to move or otherwise be adjusted between a plurality of different second configurations with different diameters (e.g., move between different diameters to accommodate a range of different sized vasculature).

Wires 52 depicted in FIGS. 1A-2 can spiral or subtends in a predetermined manner. Wires 52 can be oriented obliquely relative to axis 25 of catheter 10. Throughout this disclosure, the term "obliquely" is intended to mean that a plane in space that best fits the shaped one or more wires 52 and angled relative to axis 25. An angle $\theta$ between the plane P and the axis 25 can range between about 45 to 105 degrees, preferably between about 75 to 105 degrees, and more preferably about 90 degrees. Section 14 can include an elongated member that extends along a longitudinal axis (e.g., axis 25), the elongated member having a circumferential opening 22 disposed on an outer surface of the elongated member. Opening 22 can be provided from which mechanism 50 can be distally translated until expanded in the second configuration, as more clearly seen in FIG. 1B. Once expanded, mechanism 50 is capable of anchoring against a blood vessel wall (e.g., pushing into the blood vessel wall) such as a coronary sinus wall. In some examples, the one or more wires 52 can include a sensor to detect contact force with the vessel wall during the process of anchoring to ensure a predetermined force is achieved for anchoring. Alternatively, the sensor can be used to ensure a predetermined force is not exceeded to avoid rupturing the corresponding vessel wall.

Prior to being deployed, mechanism 50 can be in the first configuration contained within a lumen of the catheter 10. For example, the one or more wires 52 of mechanism 50 can be positioned internal to a lumen of catheter 10 (e.g., lumen 22). One or more wires 52 can also be coextensive with catheter 10. In certain examples, lumen associated with opening 22 can be formed by a slit selectively positioned with the outer surface of catheter body 12 at tip section 14 so as to provide spacing for the one or more wires 52 to be deployed therefrom. In some examples, mechanism 50 can be attached to or otherwise be in the second configuration on only one side of an outer surface of the catheter 10 so as to be pushed against the blood vessel wall on the lone side.

Figure 3A:
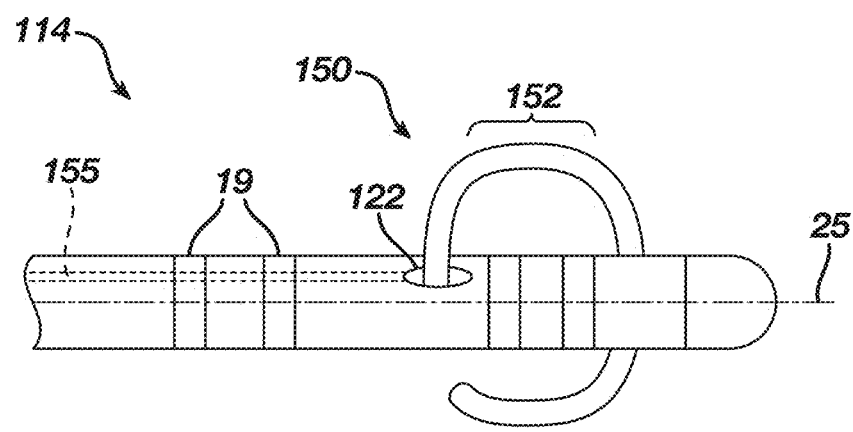
FIG. 3A is a close-up side view of a portion of a tip section of another example catheter of this disclosure.
Figure 3B:
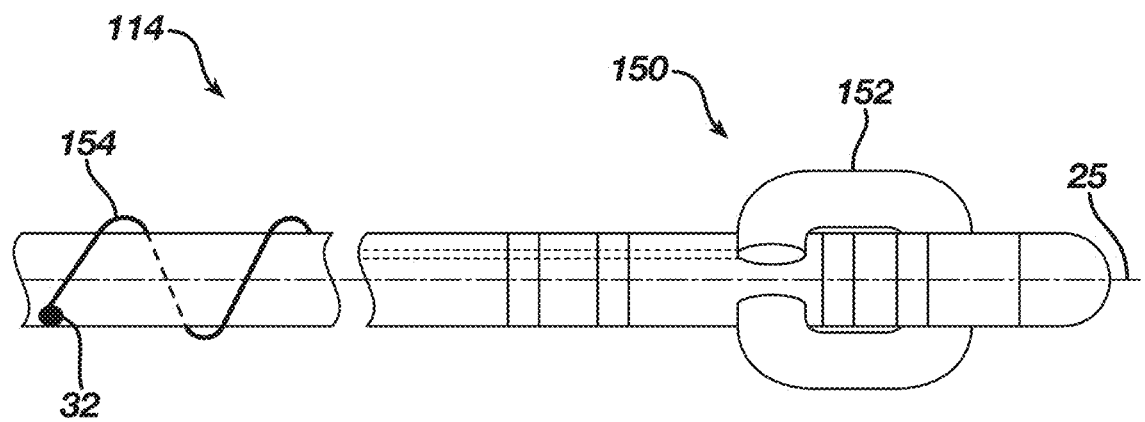
FIG. 3B is another close-up side view of the portion of the tip section of FIG. 3A.

FIG. 3A is a close-up side view of a portion of a tip section 114 of another example catheter. FIG. 3B is another close-up side view of the portion of the tip section 114 of FIG. 3A in a second configuration. In this example, mechanism 150, similar to mechanism 50, is extendable and/or deployable via opening 122 that is positioned on an outer surface of or adjacent section 114. Mechanism 150 can include one or more segments 152 (e.g., wires or other biocompatible materials) that form one or more loop segments 153, similar to previously described mechanism 50. As can be seen, one or more segments 152 can be thicker than one or more wires 52, though may not necessarily be thicker. In some examples, one or more segments 152 can include a catheter construction of a smaller diameter than the lumen of catheter 110.

As can be seen, a coiled wire 154 can be attached proximal of mechanism 50 and any corresponding one or more loop segments 153. Coiled wire 154 can be configured so that twisting or otherwise moving wire 154 can cause mechanism 150 to extend and/or deploy through opening 122. In some examples, twisting or otherwise moving wire 154 can also cause mechanism 150, including any of its one or more loops 153, to anchor to the vessel wall in the second configuration, as in FIG. 3B, so a user can adjustably and precisely push mechanism 150 against the vessel wall. Wire 154 can include one or more twists on or about catheter 110 and be axially connected to catheter 110 (e.g., wrapped around an outer surface of the catheter 110). However, wire 154 is not so limited and can be attached to the outer surface and/or inner surface of catheter 110 elsewhere or differently, as needed or required. Further, in some examples, mechanism 150 can be deployed through opening by adding or removing twists for an elongate wire in the first configuration to a coiled wire 154 in the second configuration (e.g., by twisting or otherwise moving wire 154) that in turn actuates the mechanism 150 to form the one or more loops 153 and/or otherwise anchor with the vessel wall.

Figure 4A:
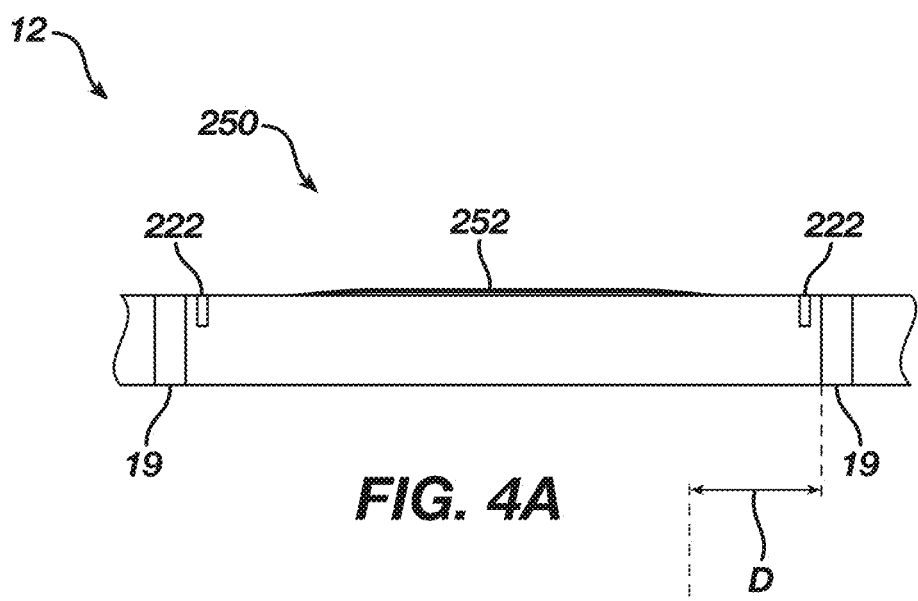
FIG. 4A is a close-up side view of a portion of a tip section of another example catheter of this disclosure.
Figure 4B:
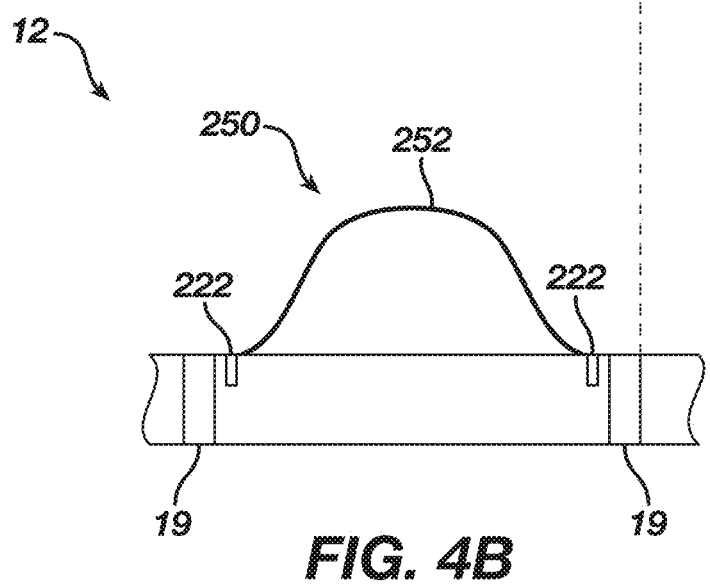
FIG. 4B is another close-up side view of the portion of the tip section of FIG. 4A.

FIG. 4A is a close-up side view of a portion of a tip section 214 of another example catheter 210 of this disclosure in the first configuration before anchoring. FIG. 4B is another close-up side view of the portion of the tip section 214 in the second configuration, whereby mechanism 250 is configured for anchoring. Mechanism 250 as shown can include one or more strips extendable and/or deployable through slits 222 in an outer surface of the catheter 210. In some examples, one or more electrodes can be included with one or more of strips 252. The one or more strips 252 can be configured to bunch up and outwardly extend when one or more portions of the distal tip section 214 are withdrawn towards one or more portions of the catheter proximal thereof, as seen between FIGS. 4A-4B, where section 214 has been shortened a distance D. Distance D can range, including be selected by a predetermined ratio with a radial extent of the one or more strips 252 in the second configuration (e.g., a 1:1 ratio, a 1:2 ratio, etc.). It is understood that any ratio can be used as needed or required for selecting the distance D to corresponding to the outward diameter required of the second configuration. The one or more strips 252 can be actuated to the second configuration by one or more pull members actuatable by an end-user operatively connected to the one or more strips 252. In some examples, one or more wires 252 and/or slits 222 can be evenly spaced strips radially in order to center catheter 210.

In some examples, one or more strips 252 can be outwardly extendable to a diameter at least two times an outer diameter of catheter 210. One or more strips 252 can be positioned on only one side of the catheter 210 and configured to push into the blood vessel on that only one side, as shown. However, it is contemplated that one or more strips 252 can be designed to extend outwardly from multiple sides of the catheter 210, similar to a balloon. One or more strips 252 can be positioned between electrodes 19, which can be one or a combination of an ablating electrode, a recording electrode, a sensing electrode, and/or the like. In some examples, one or more sensing electrodes can be included to detect movement of catheter 210 and/or whether mechanism 250 is anchored to the vessel wall. Such sensing by electrode(s) 19 can be particularly advantageous in conveying to the end-user whether mechanism 250 is sufficiently anchored or moving unnecessarily.

The region surrounding one or more strips 252 can include relatively soft and/or pliable plastic that includes an elastomer. Acceptable materials for the surrounding region can include one or a combination of polyether block amide, polyether ether ketone (PEEK), Pebax®, which can include elastomers as block copolymers made up of rigid polyamide blocks and soft polyether blocks.

Figure 5A:
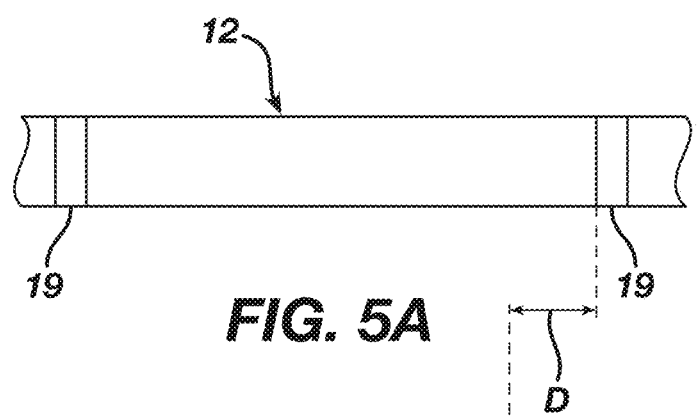
FIG. 5A is a close-up side view of a portion of a tip section of another example catheter of this disclosure.
Figure 5B:
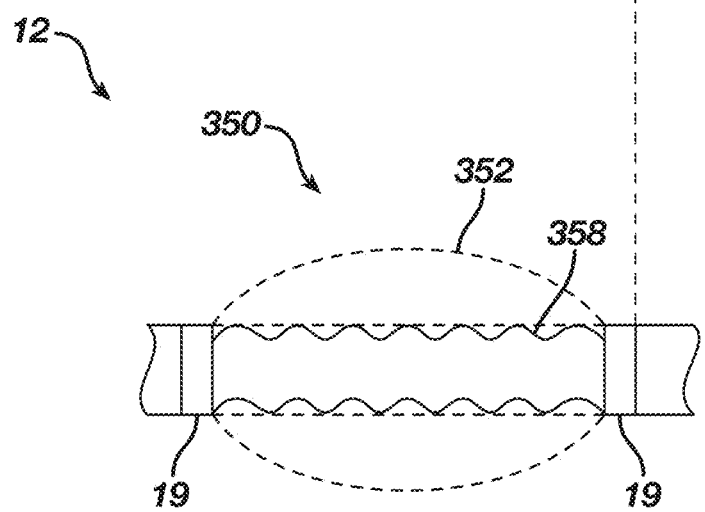
FIG. 5B is another close-up side view of the portion of the tip section of FIG. 5A.

Turning to FIG. 5A, catheter body 12 is shown in a first configuration while FIG. 5B is shown in a second configuration. Mechanism 350 is shown more clearly in FIG. 5B having been deployed via an outer surface of the catheter body 12 with one or more strips 352 bunched up and outwardly extended after one or more portions of the catheter body 12 are withdrawn distance D towards one or more portions of the catheter proximal thereof. In some examples, the anchor mechanism 350 can include a plurality of walls 352, 358. A first wall 358 can be pliable and a second wall 352 of the plurality of walls can be formed as strips more rigid than the first wall 358. For example, the less stiff, pliable first wall 358 can be made out of any low durometer Pebax, urethane, other polymer, and/or the like. In other examples, first wall 358 can be made out of a thin-walled extrusion, which can allow first wall 358 to collapse and/or crumple on itself. The rigid material can be made out of PEEK, a plastic including relatively high durometer, shape metals like nitinol, regular urethanes, Pebax and/or the like.

Walls 352 can include relatively soft and/or pliable plastic that includes an elastomer. In some examples, walls 352 are designed with softer material to permit the catheter 310 to shrink distance D thereby causing the strips of wall 352 to buckle out. The strips of wall 352 can be outwardly expandable when the section thereabout is withdrawn distance D causing the first wall 358 to crumple in on itself. Acceptable materials for walls 352 can include one or a combination of polyether block amide, and Pebax®, which can include elastomers as block copolymers made up of rigid polyamide blocks and soft polyether blocks. Walls 358 can be more rigid include polyether ether ketone (PEEK). Similar to mechanism 250, mechanism 350 can be positioned between electrodes 19, which can be one or a combination of an ablating electrode, a recording electrode, a sensing electrode, and/or the like.

Figure 6A:
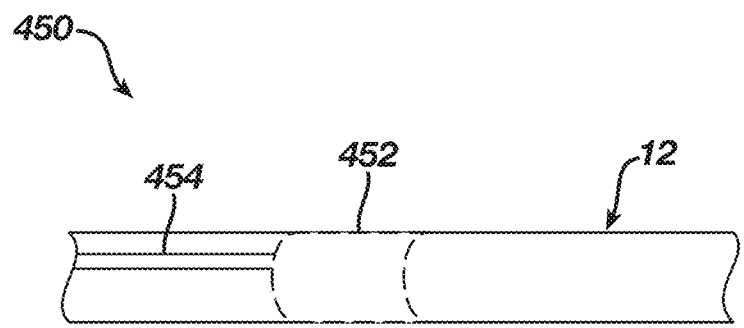
FIG. 6A is a close-up side view of a portion of a tip section of another example catheter of this disclosure.
Figure 6B:
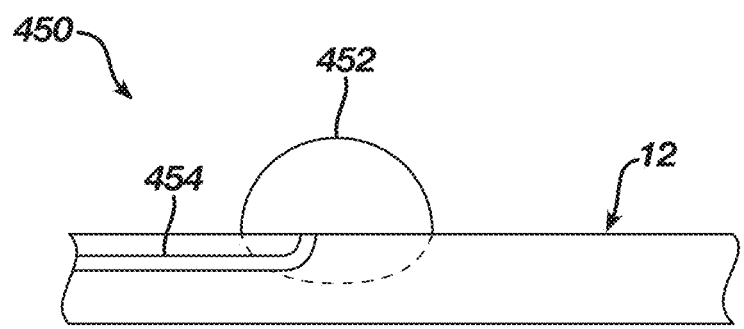
FIG. 6B is another close-up side view of the portion of the tip section of FIG. 6A.

Turning to FIG. 6A, mechanism 450 is shown in a first configuration collapsed with catheter body 12. Conversely, FIG. 6B shows mechanism 450 in a second, expanded configuration. Mechanism 450 can be provided through a relatively a soft section of region 452 whereby applied pressure thereto can cause said soft section 452 to expand and balloon outwardly. In some examples, the expandable section of region 452 can be formed with a wall of the catheter body 12 that is softer than surrounding wall sections of the catheter body 12. In some examples, pressure can be directly applied via lumen 454 which is in fluid communication with region 452 of mechanism 450. Applying pressure via lumen 454 and into region 452 can cause mechanism 450 to expand outwardly to the depicted balloon configuration of FIG. 6B. In some examples, to achieve expansion in only the one side, as shown, a stiffener or otherwise more rigid material can be added around region 452 to prevent expansion of certain radial percentage or extent. In some examples, region 452 can expand outwardly from only one side of the catheter body 12, though it is contemplated that region 452 to expand outwardly from more than one side.

Figure 7A:
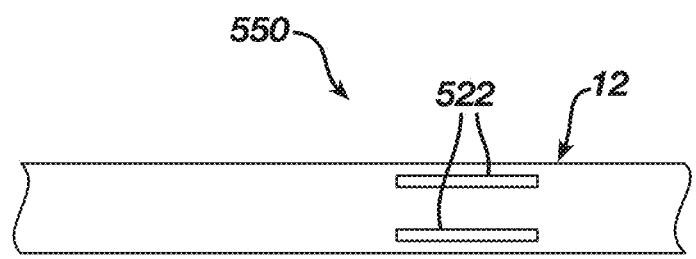
FIG. 7A is a close-up side view of a portion of a tip section of another example catheter of this disclosure.
Figure 7B:
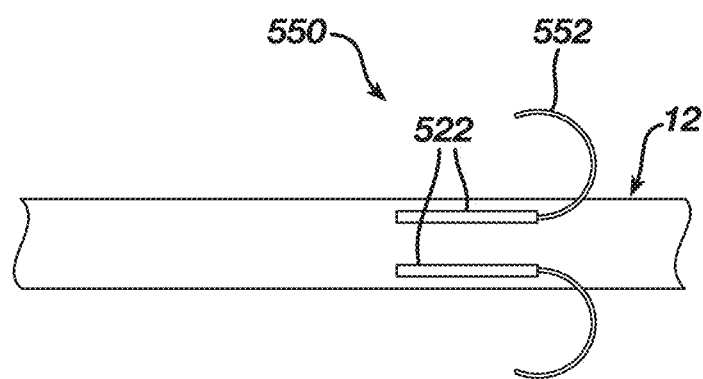
FIG. 7B is another close-up side view of the portion of the tip section of FIG. 7A.

Turning to FIG. 7A, a close-up side view of anchor mechanism 550 is shown in a first configuration pre-deployment whereas FIG. 7B illustrates mechanism 550 in the second configuration deployed from catheter body 12 and capable of anchoring to a vessel wall. Mechanism 550 can include one or more wires 552 that are shaped and configured to exit distally through one or more slits 522 or openings in catheter body 12. In the second configuration of FIG. 7B, after having been distally moved or translated a predetermined distance, one or more wires 552 can be seen in the form of fish-hook style anchors configured to push and anchor into the vessel wall. The one or more wires 552 can be retracted back into the catheter body 12 from the second configuration after being deployed. The one or more wires 552 can also exit the respective slits 522 or openings of the catheter body 12 multiple times and secured at or adjacent the tip section. In some examples, the one or more wires 552 are deployed to the second configuration by being advanced from a proximal shaft or a proximal handle operatively coupled to a proximal end of the catheter 10.

One or more wires 552 can be shape-set and be connected, directly or indirectly, to a pull wire mechanism configured to retract one or more wires 552 into catheter body 522 when not in use and deploy from slits 522 or openings for use. While one or more wires 552 are seen with fish-hook type shapes, alternate wire shapes for less traumatic anchoring are contemplated. One or more wires 552 can be positioned on only one side of an outer surface of the catheter body 12 to anchor against the blood vessel wall or multiple sides as shown in FIG. 7B.

Figure 8A:
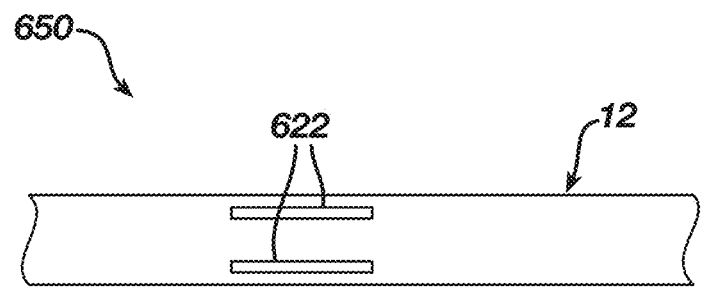
FIG. 8A is a close-up side view of a portion of a tip section of another example catheter of this disclosure.
Figure 8B:
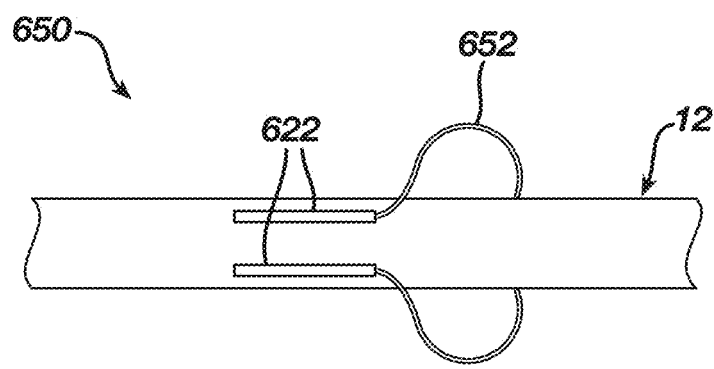
FIG. 8B is another close-up side view of the portion of the tip section of FIG. 8A.

Turning to FIG. 8A, a close-up side view of anchor mechanism 650 is shown in a first configuration pre-deployment whereas FIG. 8B illustrates mechanism 650 in the second configuration deployed from catheter body 12 and capable of anchoring to a vessel wall. Mechanism 650 can include one or more wires 652 that are shaped and configured to exit distally through one or more slits 622 or openings in catheter body 12. In the second configuration of FIG. 8B, after having been distally moved or translated a predetermined distance, one or more wires 652 can be seen in bulged with at least one anchoring bump. The at least one anchoring bump of one or more wires 652 in the second configuration of FIG. 8B can include a collective diameter at least two times greater than an outer diameter of the catheter body 12.

The at least one anchoring bump of one or more wires 652 can include an atraumatic surface configured to contact the vessel wall during anchoring. The one or more wires 652 can be retracted back into the catheter body 12 from the second configuration after being deployed. The one or more wires 652 can also exit the respective slits 622 or openings of the catheter body 12 multiple times and secured at or adjacent the tip section. In some examples, the one or more wires 652 are deployed to the second configuration by being advanced from a proximal shaft or a proximal handle operatively coupled to a proximal end of the catheter 10.

Figure 9A:
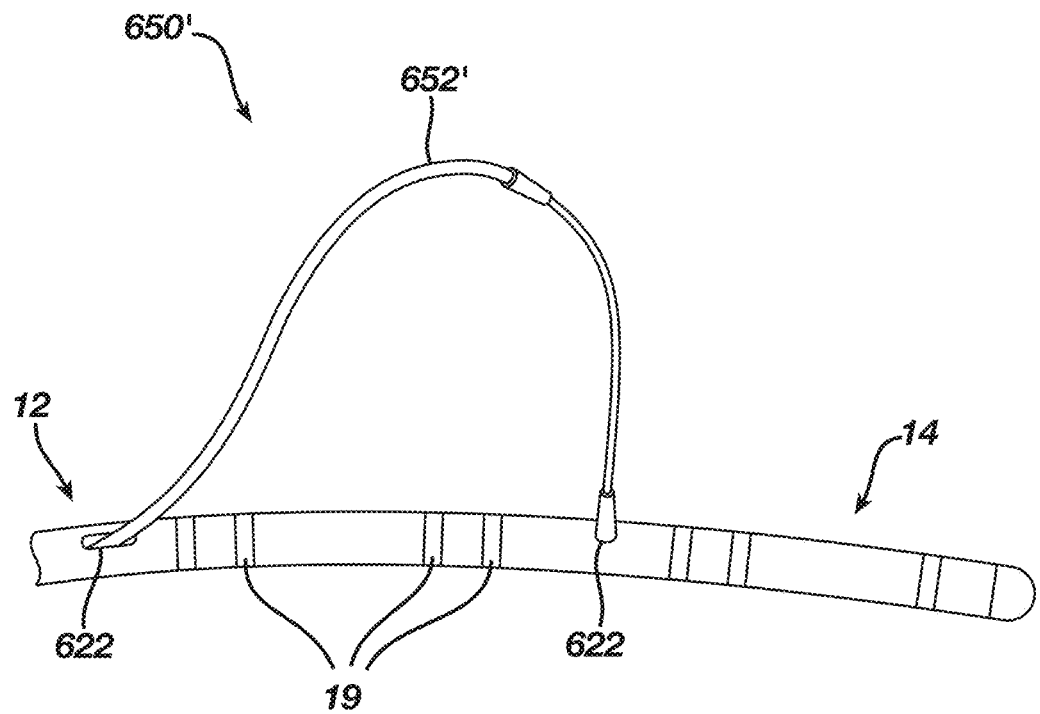
FIG. 9A is a close-up side view of an alternative portion of the tip section of FIG. 8A.

Turning to FIG. 9A, a close-up side view of an anchor mechanism 650' is shown. In particular, mechanism 650' of FIG. 9A is illustrated in the second configuration having been deployed and expanded. One or more electrodes 19 are provided between slits or openings 622 whereby 650' is shown having been deployed asymmetrically on only one side of catheter body 12. In the depicted configuration, wire 652' is shown having been urged outwardly by having its proximal end (not shown) moved distally so as to buckle outward wire 652' into the second configuration. Wire 652' can be fixed at one or more points (e.g., at the distal slit or opening 622). In moving between first and second configurations, some or all of wire 652' can be configured to contact and anchor into the corresponding vessel wall. An expanded diameter of wire 652' can also be manipulated by translating wire 652' distally or proximally as needed or required.

Figure 9B:
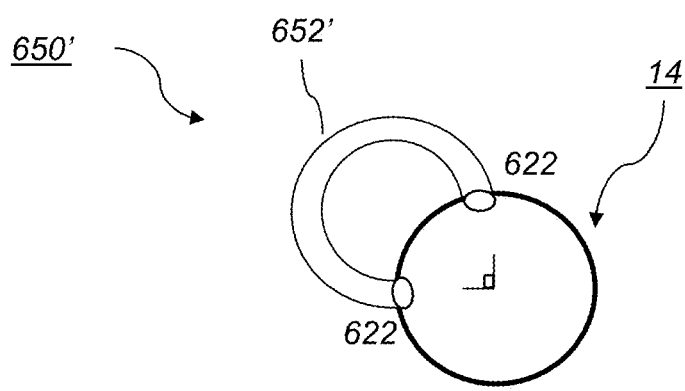
FIG. 9B is a close-up cross section view of the tip section of FIG. 9A.

Advantageously, by providing an exit point of wire 652' and distal fixed point oriented by angle A of approximately 90 degrees with each other in the second configuration, the amount of force needed to push out the wire is significantly reduced, which is desirable since less force is required to actuate between configurations and thus increased deployment control with reduced force transmitted to the patient. It should be understood that mechanism 650, oriented as defined by angle A, in an orthogonal configuration may not necessarily be preferable or even optimal, but having the exit point and end points in-line as depicted can create a more nearly axial transmission of force down the wire 652', requiring more force to buckle, whereas off-axis buckles more readily. Additionally, having the plane that is coincident with parabolic shape formed by the extended wire 652' more parallel with the axis of the catheter can make for more effective anchoring. FIG. 9B is a cross-sectional view taken at the distal fixed end at or adjacent distal slit 622 showing an example orthogonal angle A defined between extended wire 652' and a fixed distal end at or adjacent distal slit 622.

Figure 10A:
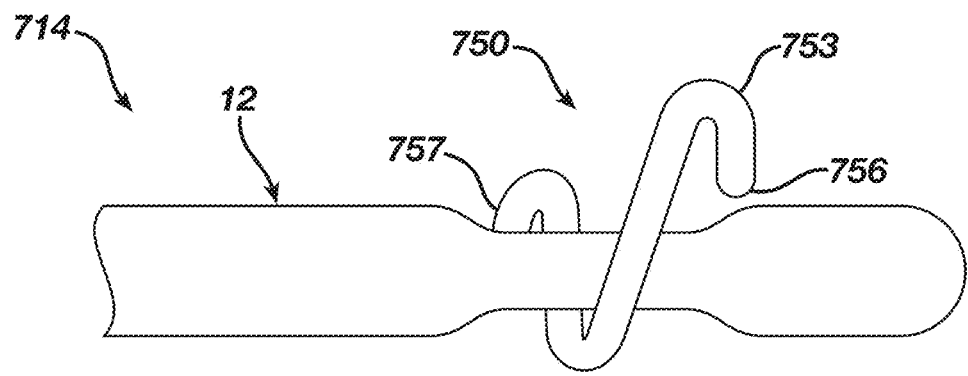
FIG. 10A is a close-up side view of a portion of a tip section of another example catheter of this disclosure.
Figure 10B:
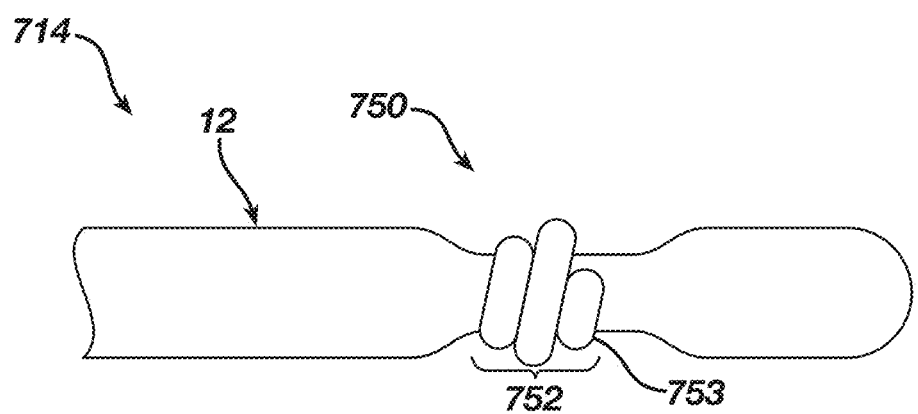
FIG. 10B is another close-up side view of the portion of the tip section of FIG. 10A.

Turning to FIG. 10A is a close-up side view of a portion of a distal tip section 714 of another example catheter. FIG. 10B is another close-up side view of the portion of the tip section 714 of FIG. 10A in a second configuration. In this example, mechanism 750, similar to prior mechanisms 50 and 150, can be deployed and undeployed by expanding and contracting its one or more variable lasso loops around body 12, similar to a python and boa constrictor. The distal end 756 of mechanism 750 can be a free-end, unattached to the catheter body 12, whereas the proximal end 757 can be attached as well as sealed with body 12. Mechanism 750 can still use a side exit but may not necessarily include an open through-way. Mechanism 750 can include one or more segments 752 (e.g., wires or other biocompatible materials) that form one or more loop segments 753, similar to previously described mechanisms 50 and 150. Outside the patient, the operator (e.g., physician) can use an actuating mechanism, such as a pull wire, that is configured to tighten the spiral(s) or loop(s) seen more clearly between FIGS. 10A-10B when moving to adjustably anchor mechanism 750 against a corresponding vessel wall. The configuration of FIG. 10A can be expandable from a corresponding delivery mechanism once released therefrom at the treatment site.

Figure 11A:
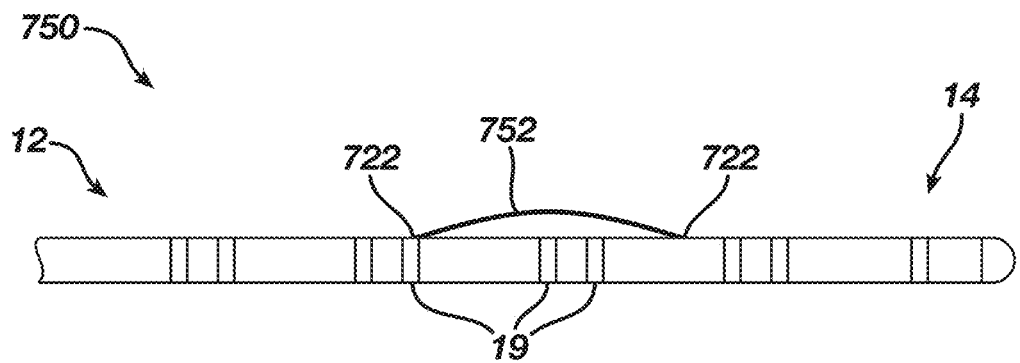
FIG. 11A is a close-up side view of a portion of a tip section of another example catheter of this disclosure.
Figure 11B:
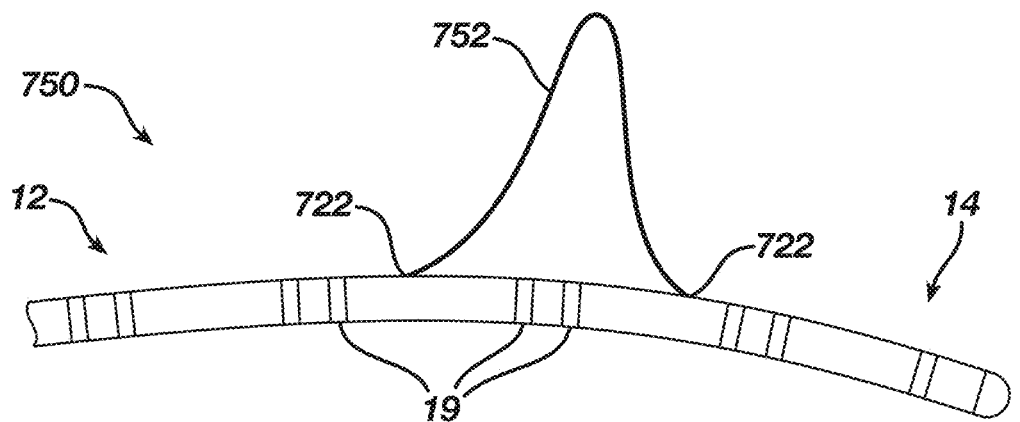
FIG. 11B is another close-up side view of the portion of the tip section of FIG. 11A.

Turning to FIGS. 11A to 11B, another example anchor mechanism 750 is shown. FIG. 11A is a close-up side view of a portion of a tip section 14 of another example catheter body 12 and corresponding mechanism 750 in a first configuration before anchoring. FIG. 11B is another close-up side view of the portion of the tip section 14 in the second configuration, whereby mechanism 750 has now expanded radially and is configured to anchor to a vessel wall, similar to FIG. 9. Mechanism 750 as shown can include one or more wires 752 expandable and/or deployable through slits or opening 722 in an outer surface of the catheter body 12.

The one or more wire members 752 can be configured to bunch up and outwardly extend through one or more portions of catheter body 12, such as one or more holes, an elongated strip or cutout, a pliable valve formed in the outer surface of the catheter body 12 through which one or more wire members 752 can deploy. In some examples, the one or more wire members 752 can impart an outward force on the blood vessel. In one example, the force applied to the vessel by the one or more wire members 752 and the friction generally between corresponding catheter 10 and tissue can anchor catheter 10 in place and resist motion in the vessel.

The one or more wire members 752 can be configured to deliver a specific force and/or include a sensor to detect contact force with the vessel wall during the process of anchoring to ensure a predetermined force is achieved for anchoring. Alternatively, the sensor can be used to ensure a predetermined force is not exceeded to avoid rupturing the corresponding vessel wall. A contact force sensor particularly suited for use with mechanism 750, as described in U.S. patent application Ser. No. 16/036,710, filed Jul. 16, 2018, and incorporated by reference herein in its entirety.

In some examples, one or more electrodes 19 can be included with one or more of wire members 752. The one or more electrodes in this example being positioned on the one or more wire members 752 can allow for multiple signals from around an inner circumference of the vessel to be taken at the same or similar depth within the vessel. In one example, deployment can be achieved by withdrawing section 14 towards one or more portions of the catheter 10 proximal thereof, as shown between FIGS. 11A to 11B where section 14 has been withdrawn causing section 14 to bow or otherwise flex.

In one example, the one or more wire members 752 are deployed by activating a puller wire that effectively reduces a distance (e.g., the shortest distance rather than the length of the wire member) between the distal and proximal end of corresponding one or more wire members 752. In some examples, the puller wire can be connected to the distal end of the one or more wire members 752. In turn, when pulled or otherwise activated, the one or more wire members 752 expand outwardly and are deployed. In some examples, a proximal portion of the one or more wire members 752 can be fixed to the catheter body 12. In this respect, when the puller wire is in a neutral location, the one or more wire members 752 can include a similar profile to the catheter body 12 (e.g., axially aligned therewith). In some examples, one or more wire members 752 can be outwardly extendable to a diameter at least four times an outer diameter of catheter body 12.

In one example, the one or more wire members 752 can be deployed by a pusher wire that runs through the catheter body 12 and is coupled to one or more wire members 752. The distal end of the pusher wire can be fixed at the distal end of the one or more wire members 752 and the proximal end can control axial translation of mechanism 750 at a corresponding handle. Anchoring of mechanism 750 in this example can be achieved by pushing the proximal end of the pusher wire in the distal direction, which can cause a length of the pusher wire and one or more wire members 752 inside the catheter body 12 to expand radially outward.

One or more wire members 752 can be positioned on only one side of the catheter body 12 and configured to push into the blood vessel on that only one side, as shown. However, it is contemplated that one or more wire members 752 can be extended outwardly from multiple sides of the catheter body 12, similar to a balloon. One or more wire members 752 can be positioned between and/or about electrodes 19, which can be one or a combination of an ablating electrode, a recording electrode, a sensing electrode, and/or the like. In some examples, one or more sensing electrodes can be included to detect movement of catheter 10 associated with catheter body 12 and/or determine whether mechanism 750 is anchored to the vessel wall. Such sensing by electrode(s) 19 can be particularly advantageous in conveying to the end-user whether mechanism 750 is sufficiently anchored or moving unnecessarily.

Figure 12A:
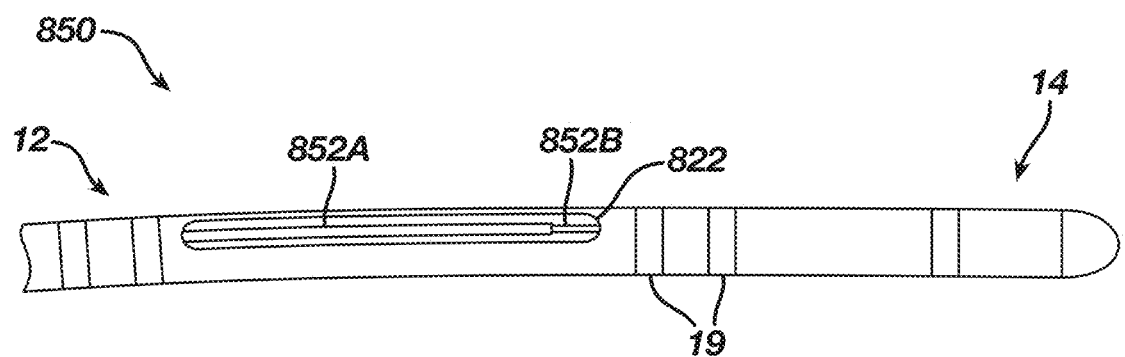
FIG. 12A is a close-up side view of a portion of a tip section of another example catheter of this disclosure.
Figure 12B:
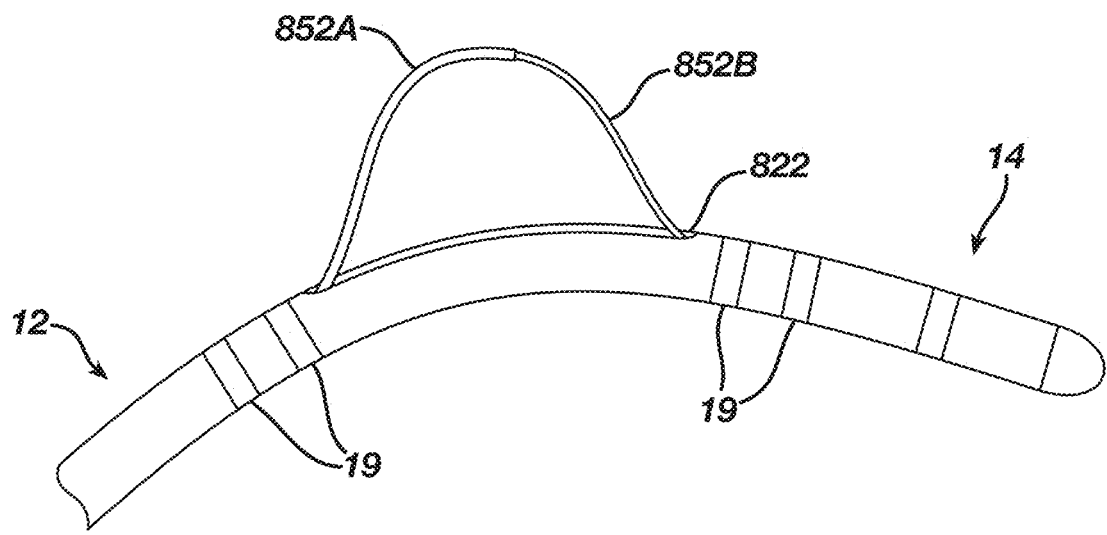
FIG. 12B is another close-up side view of the portion of the tip section of FIG. 12A.

Turning to FIG. 12A, catheter body 12 with mechanism 850 is shown in a first configuration while FIG. 12B shows catheter body 12 with mechanism 850 in a second configuration. In some examples, mechanism 850 can include an extendable member 852B that can telescope into and out of sheath member 852A between the first and second configurations. In this respect, member 852A may have a lumen with an inner diameter greater than an outer diameter of member 852B. Each of members 852A, 852B can include the same or different materials and each may be separately actuatable.

In particular, mechanism 850 is shown in FIG. 12B having been deployed through an opening 822 positioned in an outer surface of the catheter body 12. Opening 822 can be a slit that forms a one-way valve in the outer surface of catheter 12. In other embodiments, opening 822 can be substantially elliptical, rectangular, or any other shape to accommodate the first and second configurations of mechanism 850.

In some examples, member 852A can be proximally moved (e.g., pulled) while a distal end of member 852B can be fixedly attached at a distal end of opening 822. By proximal moving member 852A and/or distally moving member 852B a first distance, member 852B can expand radially, outwardly between one or more expanded states of corresponding diameter(s) greater than an outer diameter of catheter 12. In some examples, a length of member 852B previously contained with member 852A and/or catheter 12 can be released through opening 822 and radially outwardly to a corresponding vessel wall.

In some examples, the diameter of the second configuration of mechanism 850 can be as big or greater than that of a corresponding vessel diameter. One or both of members 852A, 852B can be formed with a predetermined bias (e.g., by being heat set, with a spring-like element constructed therewith, etc.) so as to cause mechanism to outwardly expand radially when member 852A is withdrawn proximally moved.

Acceptable materials for material on or adjacent opening 822 can include one or a combination of polyether block amide, and Pebax®, which can include elastomers as block copolymers made up of rigid polyamide blocks and soft polyether blocks. Similar to previous anchor mechanisms of this disclosure, mechanism 850 can be positioned between electrodes 19, which can be one or a combination of an ablating electrode, a recording electrode, a sensing electrode, and/or the like. Although not shown, members 852A, 822B may also include electrodes 19 selectively positioned and/or spaced therealong. Similarly, portions of catheter 12 adjacent opening 822 may also include one or more electrodes 19 selectively positioned and/or spaced therealong.

Figure 13A:
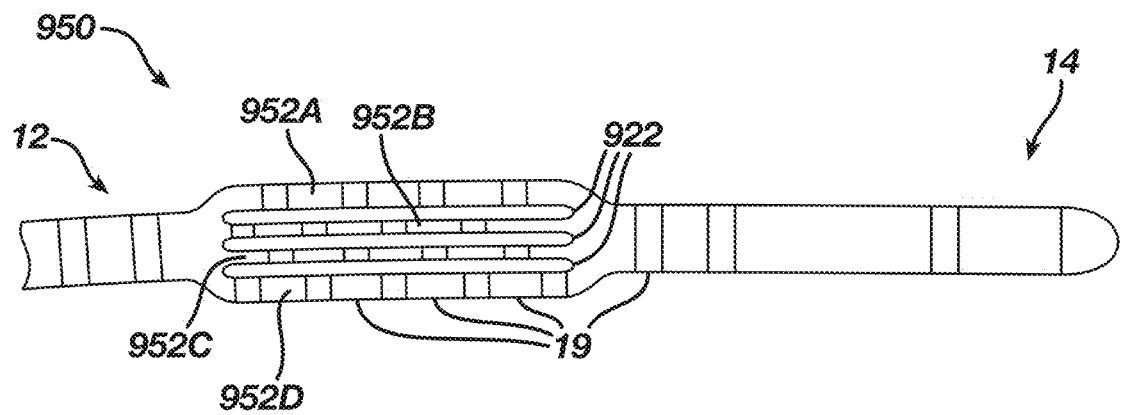
FIG. 13A is a close-up side view of a portion of a tip section of another example catheter of this disclosure.
Figure 13B:
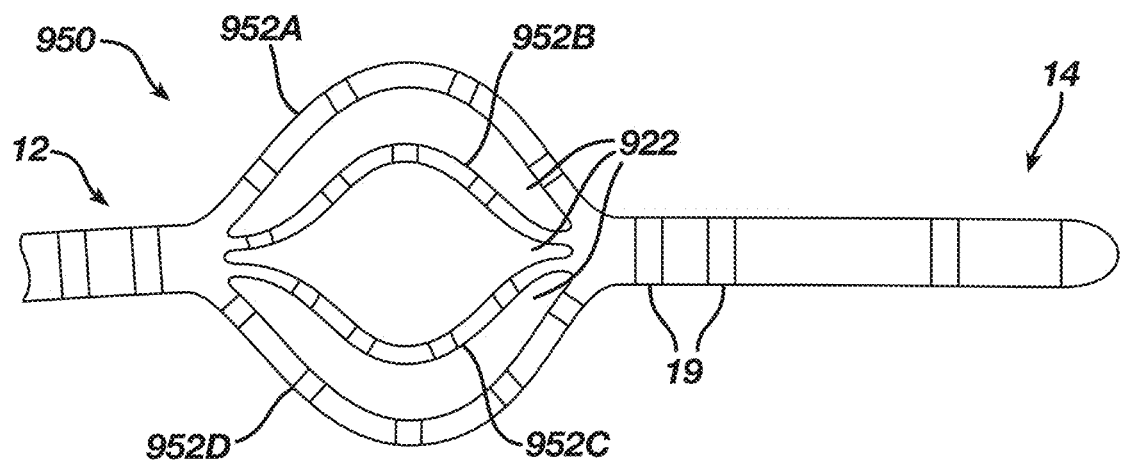
FIG. 13B is another close-up side view of the portion of the tip section of FIG. 13A.

Turning to FIG. 13A, catheter body 12 with mechanism 950 is shown in a first configuration while FIG. 13B shows catheter body 12 with mechanism 950 in a second configuration. In some examples, mechanism 950 can include flexible and/or expandable members 952A, 952B, 952C, 952D. While four (4) expandable members are shown here, fewer or greater expandable members can be included with mechanism 950 as needed or required. Members 952A, 952B, 952C, 952D can be integrally or separately formed with catheter body 12. A gap, void, or space can be positioned between respective members 952A, 952B, 952C, 952D. Each of members 952A, 952B, 952C, 952D can be radially arranged in series about the longitudinal axis of body 12. In some examples, portions of body 12 proximal of members 952A, 952B, 952C, 952D can be distally moved (e.g., pushed) while a distal tip 14 can be relatively stationary. By distally pushing body 12, members 952A, 952B, 952C, 952D are caused to deploy radially outwardly between one or more expanded states of corresponding diameter(s) greater than an outer diameter of catheter 12.

In some examples, each of members 952A, 952B, 952C, 952D can include an inner push wire (not shown) that is separately pushable by an end-user. A distal end members 952A, 952B, 952C, 952D can remain fixed or include an inner stop that prevents corresponding push wires from translating distal thereof so that further distal pushing causes respective members 952A, 952B, 952C, 952D to expand outwardly. In this instance, rather than pushing all of body 12, each of members 952A, 952B, 952C, 952D can be separately actuatable by distally moving a push wire associated with a respective member 952A, 952B, 952C, 952D.

This can be advantageous to accommodate different sized and shaped vessels to increase the amount of surface touching the vessel wall.

Members 952A, 952B, 952C, 952D can be radially arranged around a longitudinal axis of catheter body 12. Each of members 952A, 952B, 952C, 952D can have different diameters in the second configuration. In another example, each of members 952A, 952B, 952C, 952D can have the same or substantially similar diameters and expand in a balloon-like manner to form a porous, anchoring balloon on account of the gaps or voids formed between each member 952A, 952B, 952C, 952D. In another example, members 952A, 952B, 952C, 952D can spaced apart but not necessarily radially separated. For example, mechanism 950 formed by members 952A, 952B, 952C, 952D can be substantially planar or otherwise non-circular or have a shape that is different from that of the catheter body 12. Members 952A, 952B, 952C, 952D can also include one or more electrodes, which can be one or a combination of an ablating electrode, a recording electrode, a sensing electrode, and/or the like. Similar to previous anchor mechanisms of this disclosure, mechanism 950 can be positioned between electrodes 19, which can be one or a combination of an ablating electrode, a recording electrode, a sensing electrode, and/or the like.

Figure 14:
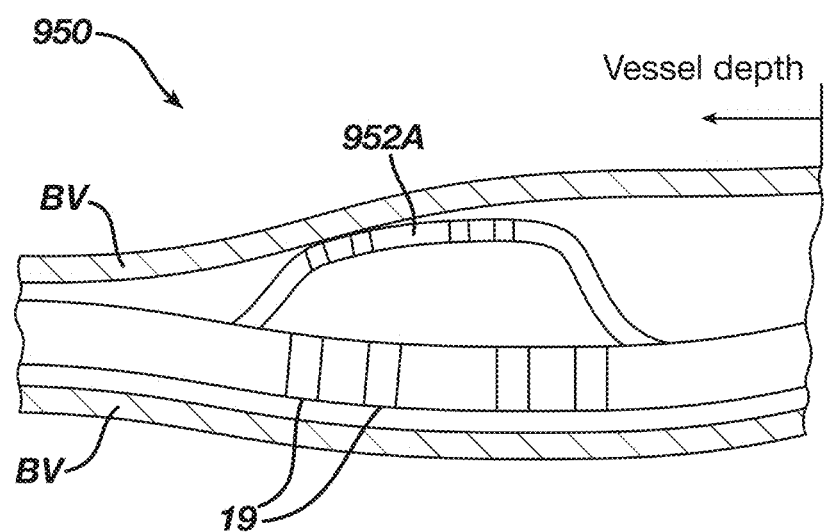
FIG. 14 is a close-up side view of a portion of a tip section of another example catheter of this disclosure expanded in an example vessel.

FIG. 14 shows mechanism 950 asymmetrically deployed in the second configuration, whereby member 952A is contacting blood vessel BV. It can be seen that member 952A in the depicted configuration can contact vessel BV along a relatively increased surface area. Moreover, electrodes of member 952A (and other expandable members not shown) can allow for multiple radial positions per electrode per respective expandable member to be read simultaneously, thereby increasing accuracy and precision sensed information, as opposed to existing catheters that only record one radial position at a given vessel depth. For ease of reference and not with limitation, FIG. 14 denotes an example definition of what "vessel depth" can mean for purposes of this disclosure.

Figure 15A:
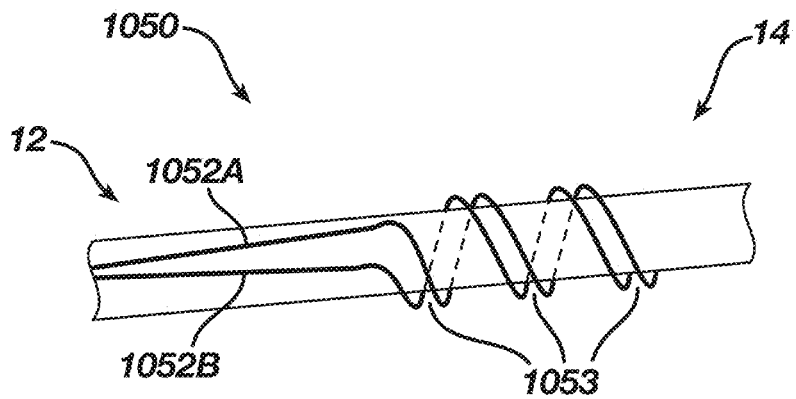
FIG. 15A is a close-up side view of a portion of a tip section of another example catheter of this disclosure.

Turning to FIG. 15A is a close-up side view of a portion of anchor mechanism 1050 of another example catheter body 12. In this example, mechanism 1050 can be actuated by translating mechanism 1050 distally via pusher wire 1056 as its one or more loops 1053 are relatively stationary or fixedly wrapped on or adjacent the distal tip section 14. In another example, mechanism 1050 can be actuated between first and second configurations by expanding and contracting its one or more variable lasso loops 1053 around body 12, similar to a python and boa constrictor. Wire 1056 of mechanism 1050 can be positioned within a lumen of catheter body 12 and exit through a side exit 1022 of catheter body 12 distally until running to convergence 1057. Distal of convergence 1057, a pair of expandable members 1052A, 1052B can run generally parallel distal towards tip 14. Members 1052A, 1052B can include one or more wires or other biocompatible materials that together, with other corresponding members that form one or more loop segments 1053, similar to previously described mechanisms 50 and 150. In another example, mechanism 1050 may not necessarily be positioned within a lumen of body 12 or exit through an exit of body 12 but instead may generally run along an outer surface of catheter body 12.

Figure 15B:
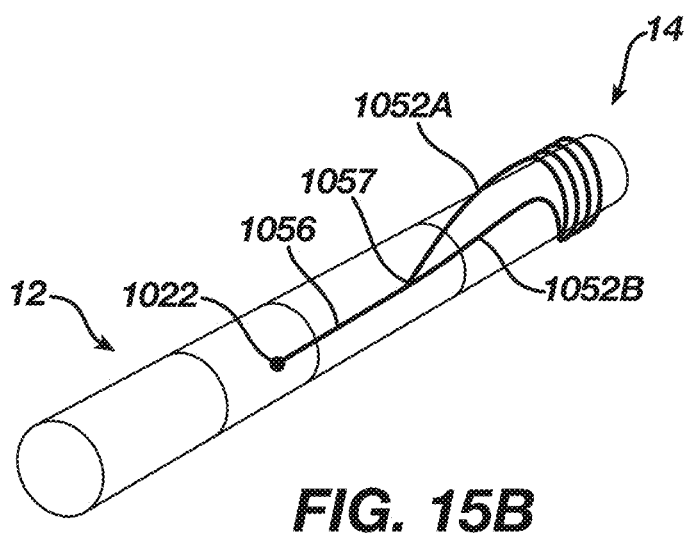
FIG. 15B is a close-up perspective view of the portion of the tip section of FIG. 15A.
Figure 15C:
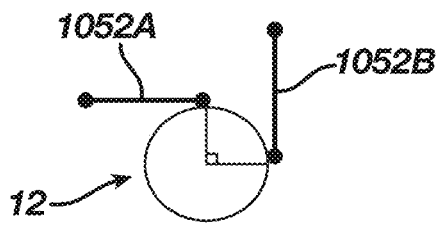
FIG. 15C is a close-up plan view of the portion of the tip section of FIG. 15A in a first orientation.
Figure 15D:
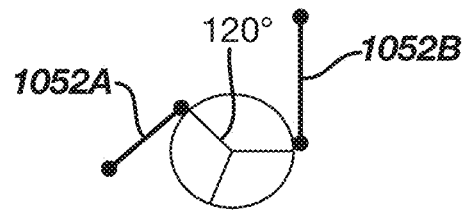
FIG. 15D is a close-up plan view of the portion of the tip section of FIG. 15A in a second orientation.

Outside the patient, the operator can actuate mechanism 1050, such as by pushing or pulling mechanism 1050, so as to tighten the spiral(s) or loop(s) seen more clearly between FIGS. 15A-15B when moving to adjustably anchor mechanism 1050 against a corresponding vessel wall. In particular, FIG. 15B shows members 1052A, 1052B expanded radially outward as loops 1053 are fixed against tip 14 and portions of mechanism 1050 proximal of members 1052A, 1052B are pushed distally causing this radial, outward expansion for vessel anchoring. FIGS. 15C and 15D merely show members 1052A, 1052B in exemplary front plan cross sectional view from FIG. 15B taken between convergence 1057 and loops 1053 whereby members 1052A, 1052B are radially, outwardly expanded. It can be seen that in FIG. 15C, members 1052A, 1052B are generally orthogonal with the other whereas in FIG. 15D an approximately 120 degree angle is formed between members 1052A, 1052B. Such orientations between members 1052A, 1052B can be adjusted as needed or required depending on movement proximal of members 1052A, 1052B and any corresponding actuation on loops 1053 that result in twisting.

Figure 16:
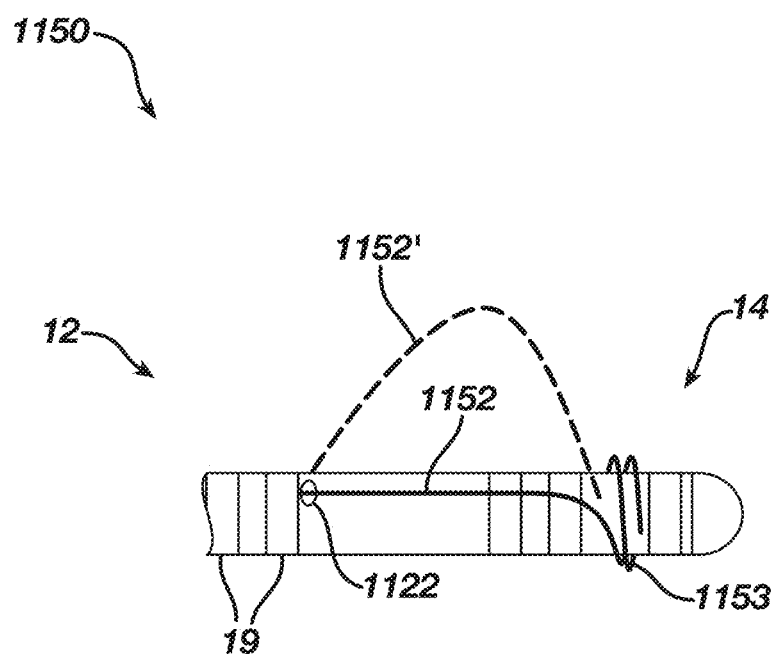
FIG. 16 depicts a close-up side view of a portion of an anchor mechanism.

FIG. 16 depicts a close-up side view of a portion of an anchor mechanism 1150, similar to mechanism 1050. In this example, mechanism 1150 can be deployed and undeployed pushing or pulling mechanism 1150 as its one or more variable lasso loops 1153 fixedly wrap around body 12, similar to mechanism 1050. Mechanism 1150 can be positioned within a lumen of catheter body 12 and exit through opening 1122 of catheter body 12 distally. Distal of opening 1122, one or more expandable members 1152 can run generally parallel distal towards tip 14. The one or more members 1152 can include one or more wires or other biocompatible materials that together, with other corresponding members that form one or more loop segments 1153, similar to previously described loop segments 1053. In turn, segments 1153 can fix the distal end of mechanism 1150 into the outer surface of tip 14. Outside the patient, the operator can actuate mechanism 1150, such as by pushing mechanism 1150 so as to cause mechanism 1150 to expand radially, outwardly as denoted by now expanded member 1152' in dashed lines in the second configuration.

In particular, FIG. 16 shows member 1152 (first configuration) and member (second configuration) 1152' after it has expanded radially outward as loops 1153 are fixedly wrapped around tip 14 causing the radial, outward expansion of mechanism 1150. Members 1152, 1152' may also include electrodes selectively positioned and/or spaced therealong. Similarly, portions of catheter body 12 adjacent opening 1122 and/or loops 1153 may also include one or more electrodes 19 selectively positioned and/or spaced therealong, which can be one or a combination of an ablating electrode, a recording electrode, a sensing electrode, and/or the like.

Turning to FIG. 17A is a close-up top view of a portion of anchor mechanism 1250 of another example catheter body 12, whereby the solid lines of expandable members 1252 correspond to the first configuration whereas the dashed lines of expandable members 1252' correspond to the second, expanded configuration. The upper and lower arrows between members 1252, 1252' are intended to denote the herein described, outward radial expansion exhibited as mechanism moves from first to second configurations. FIG. 17B shows a close-up side view of mechanism 1250 in the first, collapsed configuration taken along section A-A of FIG. 17A. FIG. 17C shows a perspective view of mechanism 1250 with members 1252, 1252' in their respective configurations.

In particular, FIGS. 17A and 17C show that mechanism 1250 can run from a lumen of catheter body 12 through an opening 1222A positioned in an outer surface of the catheter body 12. Opening 1222A can be an aperture that forms a one-way valve in the outer surface of catheter body 12. In other embodiments, opening 1222A can be substantially elliptical, rectangular, or any other shape to accommodate members 1252, 1252' running therethrough. A distal end of members 1252, 1252' can be fixedly attached at end 1222B of catheter body 12.

In some examples, member 1252 can be pushed distally while its distal end is fixedly attached at end 1222B thereby actuating member 1252 causing it to expand radially, outwardly to its depicted second configuration as member 1252'. FIG. 17D shows one example side view taking along section A-A as to fixing distal end 1255 of members 1252, 1252' to end 1222B. As shown, end 1255 can be oriented or otherwise run from an outer surface of catheter body 12 and ultimately attached to and/or within a lumen 1243 of catheter body 12. Catheter body 12 may include a plurality of lumens whereby lumen 1243 is configured to fixedly attach with end 1255. End 1255 can be soldered, welded, bonded, adhered, and/or mechanically etched into lumen 1243, though other attachments, including use of connectors, are contemplated as needed or required. In some examples, members 1252, 1252' can be heat set or otherwise configured with a predetermined bias so that the depicted shape flexes radially, outwardly to a corresponding vessel wall.

In some examples, the diameter of the second configuration of mechanism 1250, as denoted by member 1252', can be as big or greater than that of a corresponding vessel diameter. Members 1252, 1252' may also include electrodes 1219 selectively positioned and/or spaced therealong. Similarly, portions of catheter body 12 adjacent opening 1222A and/or end 1222B may also include one or more electrodes 19 selectively positioned and/or spaced therealong, which can be one or a combination of an ablating electrode, a recording electrode, a sensing electrode, and/or the like. Acceptable materials for material on or adjacent opening 1222A can include one or a combination of polyether block amide, and Pebax®, which can include elastomers as block copolymers made up of rigid polyamide blocks and soft polyether blocks. FIG. 17E shows a view of mechanism 1250 in the second configuration and similarly taking along section A-A, whereby member 1252' has expanded radially, outwardly to an example shape.

Figure 18:
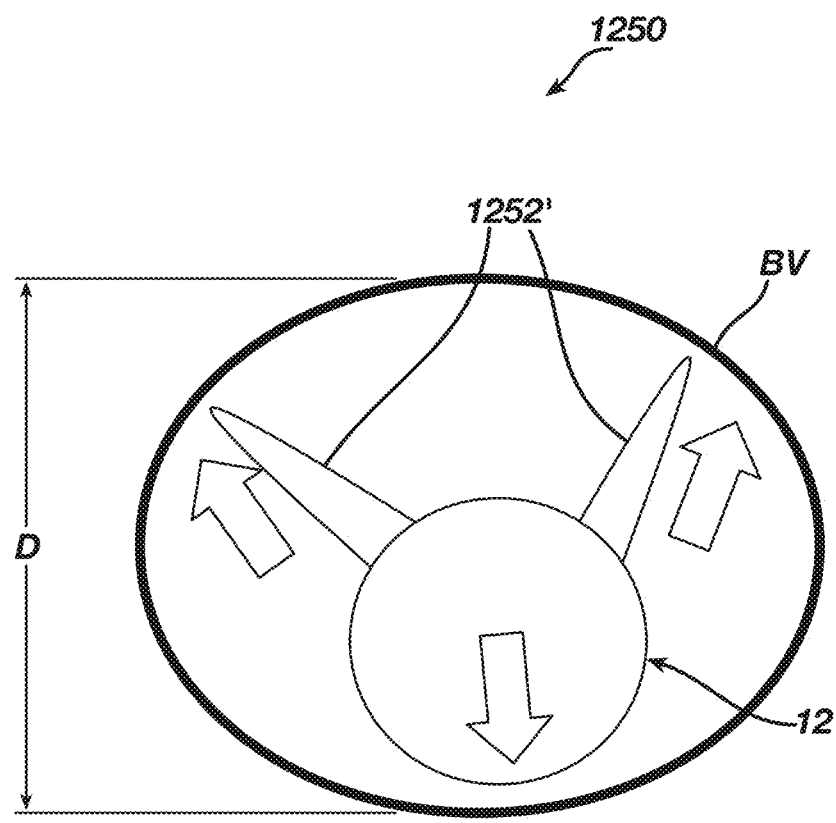
FIG. 18 a front plan view of an anchor mechanism in a second configuration in an example blood vessel.

Turning to FIG. 18, a front plan view of mechanism 1250 is shown in a second configuration in an example blood vessel BV with a diameter D. In some examples, vessel BV can be the Coronary Sinus (CS), which can vary in shape, for example by or through member 1252', being sometimes tubular and sometimes funnel shaped, depending on the patient. Vessel BV can also vary in size and be relatively pliable, so any anchoring device should expand to larger than the natural vessel diameter for sufficient anchoring. Preferably, mechanism 1250 can include range of diameters D between approximately 2 to 15 mm, though other diameters larger (e.g., up to 25 mm) or smaller are contemplated as needed or required.

It can be seen that mechanism 1250 in the second configuration has two expanded segments formed by member 1252' and anchoring with the wall of blood vessel BV. However, fewer or greater number of expanded segments are contemplated as needed or required. In some examples, a portion of catheter body 12 opposite members 1252' (e.g., the lower end, opposite the "upper" end of members 1252' of FIG. 18) can be caused to move towards and anchor with the wall of blood vessel BV as a result of mechanism 1250 expanding and member 1252' moving the opposite direction.

Figure 19:
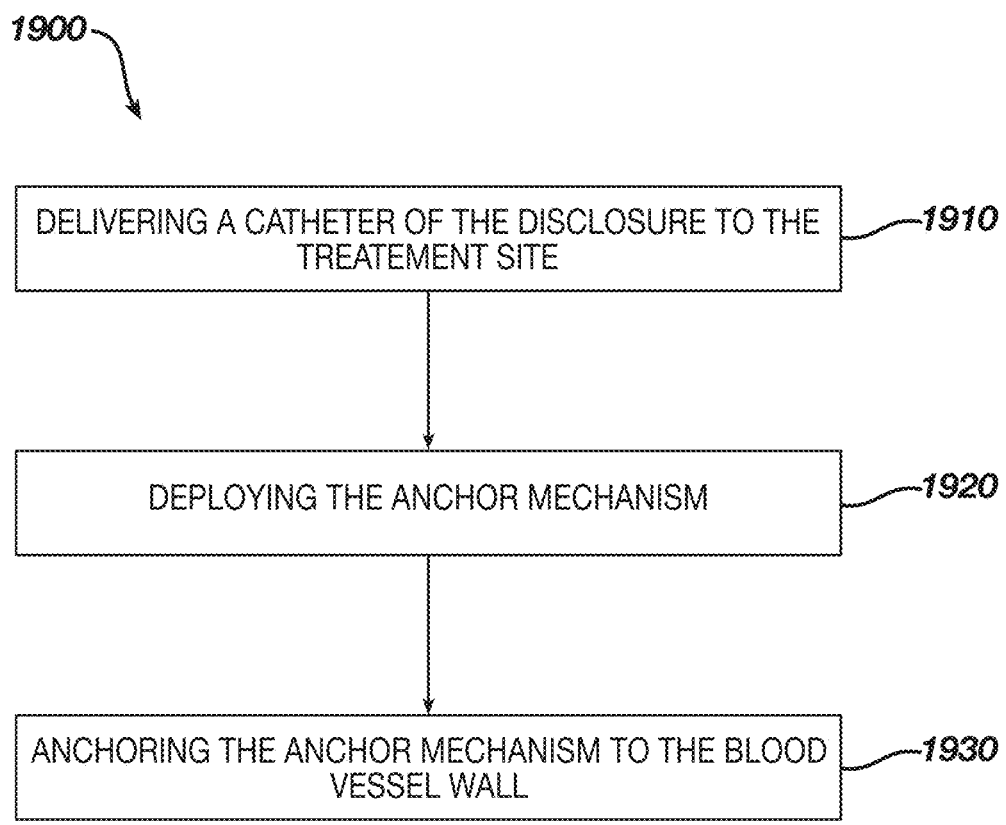
FIG. 19 is a flow diagram illustrating an example method of ablating tissue.

Turning to FIG. 19, a flow diagram is provided illustrating an example method 1900 to anchor a catheter to a blood vessel of a treatment site. The method 1900 can include step 1910 delivering any catheter of this disclosure to the treatment site. Step 1920 can include deploying the anchor mechanism. Step 1930 can include anchoring the anchor mechanism to the blood vessel wall. Other steps can be included with the method as discussed throughout this disclosure.

Figure 20A:
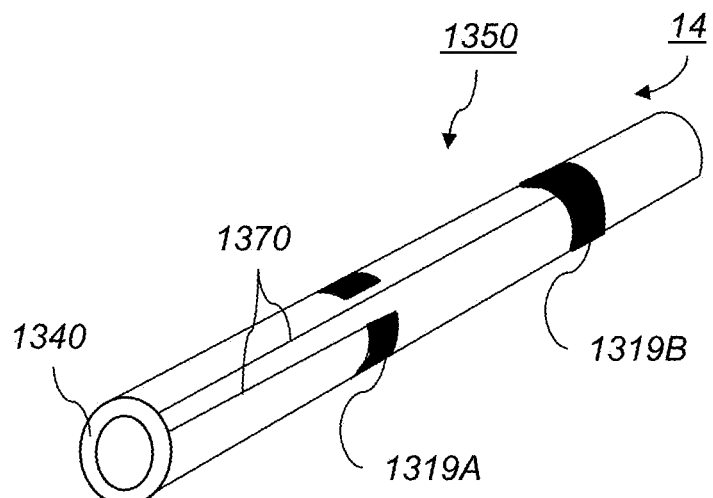
FIG. 20A shows a perspective view a portion of a tip section of another example catheter of this disclosure.
Figure 20B:
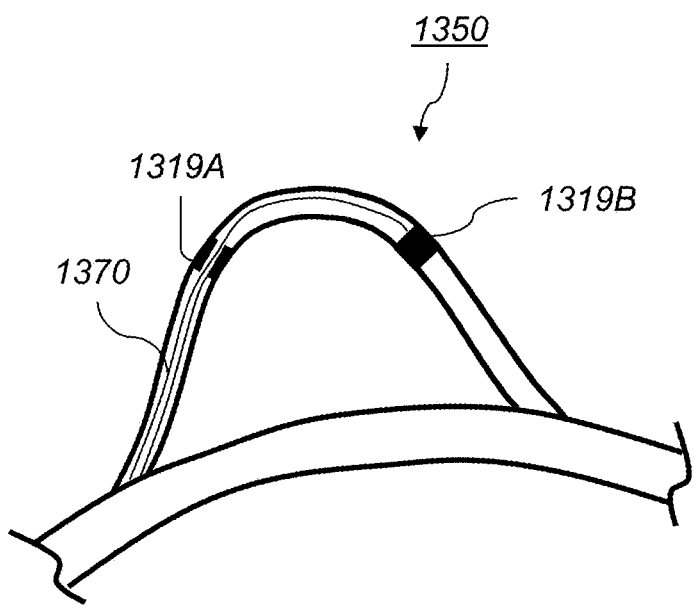
FIG. 20B is another close-up side view of the portion of the tip section of FIG. 20A.

FIG. 20A shows a perspective view a portion of a tip section of another example catheter of this disclosure with an example mechanism 1350. Mechanism 1350 can include printed electrodes 1319A, 1319B printed on cover 1340, whereby cover 1340 with corresponding printed electrodes can be positioned over mechanism 1350. One or more traces 1370 can be provided in communication with corresponding electrodes 1319A, 1319B. FIG. 20B shows mechanism 1350 expanded radially in a second configuration. Mechanism 1350 as shown is particularly advantageous for use in printing flex circuits on spin covers 1340 used with mechanism 1350.

Figure 21:
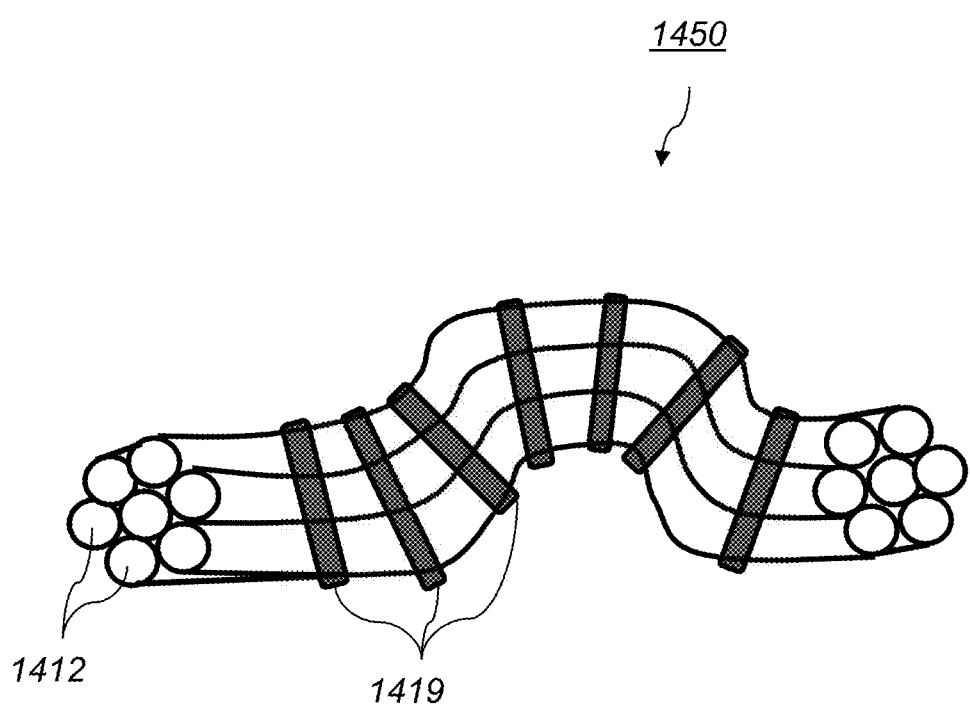
FIG. 21 shows a perspective view a portion of a tip section of another example catheter of this disclosure.

FIG. 21 shows a perspective view a portion of a tip section of another example catheter of this disclosure with an example mechanism 1450. Mechanism 1450 can include a plurality of insulated wires 1412 (e.g., memory alloy such as nitinol) bundled together with the same shape, as shown. One or more conductor rings 1419 can also be included to both bundle wires 1412 together as well as function similar to the heretofore described electrodes of other example mechanisms.

In some examples, the method includes determining a position and orientation of the anchor mechanism by generating a plurality of AC magnetic fields, each AC magnetic fields being at a different frequency; sensing the AC magnetic fields at a plurality of sensors proximate the distal tip section; and computing dimensions of position and orientation of a portion of the distal tip section responsive to signals representative of the generated magnetic fields and the sensed magnetic fields. In some examples, the method includes determining a position and orientation of the distal tip section by generating a plurality of AC magnetic fields, each AC magnetic fields being at a different frequency; sensing the AC magnetic fields at a plurality of sensors proximate the distal tip section; and computing dimensions of position and orientation of a portion of the distal tip section responsive to signals representative of the generated magnetic fields and the sensed magnetic fields.

In some examples, the method includes generating, by at least one field generator, an externally applied magnetic field to establish a frame of reference, positioning a plurality of sensors comprising single-axis coils around the distal tip section, each single-axis coils being fixed at different, respective points about the distal tip section, and determining dimensional translational and orientational coordinates of the single-axis coils by processing signals from the single-axis coils. In some examples, the method includes positioning one or more electrodes on the distal tip section at known fixed locations with respect to at least one of said single-axis coils, a location of the respective electrode being derived from the dimensional translational and orientation coordinates of the single-axis coils. Specific instrumentalities of these embodiments can be understood as including features more clearly described in Appendix 1 attached herewith, which includes U.S. Pat. Nos. 6,690,963 and 8,926,528.

In some examples, the method includes deflecting the tip section in response to moving one or more puller wires. In some examples, the method includes moving, by a steering assembly, the one or more puller wires. In some examples, the method includes deflecting the tip section in the direction of the off-axis lumen in which a respective puller wire extends. In some examples, the method includes assembling the catheter with a control handle comprising a deflection knob, and adjusting, by rotating the deflection knob, a tip deflection orientation of the tip section. In some examples, the method includes extending a segment of the one or more puller wires drawn by a pulley for deflection at an angle of less than about 7 degrees with respect to a longitudinal axis. Specific instrumentalities of these embodiments can be understood as including features more clearly described in Appendix 1 attached herewith, which includes U.S. Pat. No. 8,348,888.

Further, ECG signals may be separately assessed by electrodes of electrode catheters such that the user or the system can determine that the distal tip section has contacted tissue, and, in those embodiments with electrodes, to determine which electrodes to activate for providing ablation therapy may require stabilized catheters anchored effectively to the corresponding blood vessel wall. Contact with tissue may also be determined using force contact sensors, e.g., as described in U.S. Patent Pub. No. 2018/0256247, filed Mar. 8, 2017, which is incorporated by reference herein in its entirety. A contact force sensor particularly suited for use in a catheter having a split tip is now described, and also described in U.S. Patent Pub. No. 2020/0015693, filed Jul. 16, 2018, and incorporated by reference herein in its entirety.

In some examples, the systems and methods of use thereof described herein can be used with a pacemaker lead technology, such as with one or more fixation mechanisms to secure one or more corresponding electrodes to a vessel wall.

The anchor mechanism, in any of the foregoing embodiments, may be included on a distal tip section of a catheter. The catheter may also include an elongate body having one or more lumens disposed longitudinally therethrough. The catheter may be used according to the following method and variations. First, the catheter may be inserted into a subject, e.g., a human subject, proximate to the subject's heart with one or more of its electrodes maneuvered into contact with the tissue. The catheter may be an aspect of an ablation system that also includes a processor. Sectors and corresponding electrodes of the distal tip of the catheter can measure temperature and provide temperature data to the processor. Ablation energy may be provided to thereto as well, e.g., as controlled by the processor. One or more electrodes can be included with any of the herein discussed catheters, as shown and previously described.

What is claimed is:

1. A catheter, comprising:
   a catheter body;
   a distal tip section comprising an elongated member that extends along a longitudinal axis; and
   an anchor mechanism disposed along an outer surface of the elongated member and/or within the elongated member in a first configuration and the anchor mechanism configured to slide longitudinally along the longitudinal axis and extend radially outward with respect to the longitudinal axis adjacent at least a portion of the distal tip section in a second configuration, the anchor mechanism comprising:
   one or more wires being outwardly extendable through one or more slits formed in a distal end of the catheter on or adjacent the distal tip section to form one or more wire anchors, a distal end of the one or more wires being fixedly attached to the distal tip section and each of the one or more slits extending along a side of the catheter body in a direction along the longitudinal axis, the distal tip section being configured to move proximally along the longitudinal axis thereby causing the one or more wires to extend radially outward from the one or more slits and cause the anchor mechanism to transition from the first configuration to the second configuration.

2. The catheter of claim 1, the anchor mechanism transitioning from first to second configurations causes the catheter to bow or flex outwardly in the second configuration and deliver a predetermined force with a vessel wall.

3. The catheter of claim 1, the one or more wires being asymmetrically positioned on only one side of an outer surface of the catheter to anchor against a vessel wall.

4. The catheter of claim 1, the one or more wires in the second configuration comprising a diameter at least four times greater than an outer diameter of the catheter.

5. The catheter of claim 1, the elongated member comprising a circumferential opening disposed on an outer surface of the elongated member, the anchor mechanism configured to extend outward radially from the circumferential opening of the elongated member.

6. The catheter of claim 1, wherein at least one of the one or more wires further comprises a force sensor configured to detect a force applied to the at least one of the one or more wires.

7. The catheter of claim 1, wherein a distal end of at least one of the one or more wires is fixedly attached to the distal tip at an angle around a circumference of the catheter body with respect to a proximal portion of the at least one of the one or more wires.

8. A catheter, comprising:
   a catheter body;
   a distal tip section comprising an elongated member that extends along a longitudinal axis; and
   an anchor mechanism disposed along an outer surface of the elongated member and/or within the elongated member in a first configuration and the anchor mechanism configured to slide longitudinally along the longitudinal axis and extend radially outward with respect to the longitudinal axis adjacent at least a portion of the distal tip section in a second configuration, the anchor mechanism comprising:
   a plurality of expandable members adjacent the distal tip section, a void being positioned between respective expandable members of the plurality of expandable members,
   wherein moving the distal tip section toward portions of the catheter body positioned proximal of the plurality of expandable members causes the respective expandable members of the plurality of expandable members to expand radially outwardly to the second configuration greater than an outer diameter of the catheter body, each respective expandable member of the plurality of expandable members being outwardly extendable through a respective slit extending longitudinally along a side of the catheter body.

9. The catheter of claim 8, each of the expandable members expand outwardly in a balloon-manner in the second configuration to form a porous anchoring balloon.

10. A catheter, comprising:
    a catheter body;
    a distal tip section comprising an elongated member that extends along a longitudinal axis; and
    an anchor mechanism disposed along an outer surface of the elongated member and/or within the elongated member in a first configuration and the anchor mechanism configured to extend radially outward with respect to the longitudinal axis adjacent at least a portion of the distal tip section in a second configuration, the anchor mechanism comprising one or more strips connected to an outer surface of the catheter, the one or more strips being configured to bunch up and outwardly extend when one or more portions of the distal tip section are withdrawn towards one or more portions of the catheter proximal thereof, the one or more strips being outwardly extendable through a plurality of slits of an outer surface of the catheter, each slit of the plurality of slits extending along a side of the catheter body in a direction along the longitudinal axis.

11. The catheter of claim 10, the one or more strips being actuated to the second configuration by one or more pull members actuatable by an end-user operatively connected to the one or more strips.

12. The catheter of claim 10, the one or more strips being outwardly deployable through the plurality of slits of the outer surface of the catheter.

\* \* \* \* \*